(12) United States Patent
Shachaf et al.

(10) Patent No.: US 10,434,215 B2
(45) Date of Patent: Oct. 8, 2019

(54) COMPOSITIONS COMPRISING A POLYMER-PROTEIN CONJUGATE AND AN ENVIRONMENTALLY-RESPONSIVE POLYMER AND USES THEREOF

(71) Applicant: Regentis Biomaterials Ltd., Or-Akiva (IL)

(72) Inventors: Yonatan Shachaf, Haifa (IL); Aharon Wechsler, Shoham (IL)

(73) Assignee: Regentis Biomaterials Ltd., Or-Akiva (IL)

( * ) Notice: Subject to any disclaimer, the term of this patent is extended or adjusted under 35 U.S.C. 154(b) by 0 days.

(21) Appl. No.: 14/901,216

(22) PCT Filed: Jun. 26, 2014

(86) PCT No.: PCT/IL2014/050575
§ 371 (c)(1),
(2) Date: Dec. 28, 2015

(87) PCT Pub. No.: WO2014/207749
PCT Pub. Date: Dec. 31, 2014

(65) Prior Publication Data
US 2016/0296666 A1    Oct. 13, 2016

Related U.S. Application Data

(60) Provisional application No. 61/839,951, filed on Jun. 27, 2013.

(51) Int. Cl.
| A61L 27/26 | (2006.01) |
| A61L 27/52 | (2006.01) |
| A61L 27/58 | (2006.01) |
| A61L 27/18 | (2006.01) |
| A61L 27/22 | (2006.01) |

(52) U.S. Cl.
CPC ............. *A61L 27/26* (2013.01); *A61L 27/18* (2013.01); *A61L 27/225* (2013.01); *A61L 27/52* (2013.01); *A61L 27/58* (2013.01); *A61L 2430/06* (2013.01)

(58) Field of Classification Search
CPC ........ A61L 27/18; A61L 27/225; A61L 27/26; A61L 27/52; A61L 2430/06; A61L 27/58; C08L 71/02
See application file for complete search history.

(56) References Cited

U.S. PATENT DOCUMENTS

| 6,316,011 B1 * | 11/2001 | Ron ..................... | A61K 9/0007 424/401 |
| 7,842,667 B2 | 11/2010 | Seliktar et al. | |
| 2011/0052490 A1 | 3/2011 | Vogel | |

FOREIGN PATENT DOCUMENTS

| CN | 101264330 | 9/2008 |
| WO | WO 2005/061018 | 7/2005 |
| WO | WO 2011/073991 | 6/2011 |
| WO | WO 2014/207749 | 12/2014 |

OTHER PUBLICATIONS

Pluronic, from https://worldaccount.basf.com/wa/NAFTA/Catalog/ChemicalsNAFTA/pi/BASF/Brand/plur . . . , pp. 1-2, accessed Mar. 9, 2018.*
Poloxamer, from https://www.spectrumchemical.com/search/go?p=Q&lbc=spectrumchemical&uid=213864553&ts=custom&w=Poloxamer&isort=score&method=and&view=list&sli_jump=1&af=&cnt=64, pp. 1-2, accessed Mar. 9, 2018.*
Hynes et al, Overview of the Matrisome—An Inventory of Extracellular Matrix Constituents and Functions, Cold Spring Harb Perspect Biol, 2012, 4:a004903, pp. 1-16.*
Notification of Office Action and Search Report dated Dec. 29, 2016 From the State Intellectual Property Office of the People's Republic of China Re. Application No. 201480036509.X. (7 Pages) The English translation filed on Feb. 13, 2017 is considered.
Translation of Notification of Office Action dated Dec. 29, 2016 From the State Intellectual Property Office of the People's Republic of China Re. Application No. 201480036509.X. (3 Pages).
Communication Pursuant to Article 94(3) EPC dated Mar. 1, 2017 From the European Patent Office Re. Application No. 14741960.0. (4 Pages).
International Preliminary Report on Patentability dated Jan. 7, 2016 From the International Bureau of WIPO Re. Application No. PCT/IL2014/050575.
International Search Report and the Written Opinion dated Oct. 29, 2014 From the International Searching Authority Re. Application No. PCT/IL2014/050575.
Alexandridis et al. "Poly(Ethylene Oxide)-Poly(Propylene Oxide)-Poly(Ethylene Oxide) Block Copolymer Surfactants in Aqueous Solutions and at Interfaces: Thermodynamics, Structure, Dynamics, and Modeling", Colloids and Surfaces A: Physicochemical and Engineering Aspects, 96: 1-46, 1995.
Bouchot et al. "Clinical Experience With a Novel Thermosensitive Temporary Coronary Artery Occluder (LeGoo)", The Annals of Thoracic Surgery, 89: 1912-1917, 2010.

(Continued)

*Primary Examiner* — Karlheinz R. Skowronek
*Assistant Examiner* — Li N Komatsu

(57) ABSTRACT

A pharmaceutical, cosmetic or cosmeceutical composition which exhibits a reverse thermal gelation is disclosed herein, as well as a composition-of-matter comprising a crosslinked form of the composition, and a process for producing the composition-of-matter. The composition is characterized as exhibiting a shear storage modulus of at least 100 Pa at temperatures in a range of from 17° C. to 21° C., and a shear storage modulus of less than 100 Pa at a temperature of 4° C., and as being curable in a physiological medium, and/or comprises a polymer-polypeptide conjugate comprising a polypeptide having attached thereto at least two polymeric moieties, wherein at least one of said polymeric moieties further comprises at least one polymerizable group; a poloxamer; and a poloxamer substituted by at least one polymerizable group. Further disclosed herein are uses of the composition and/or composition-of-matter in the treatment of tissue damage or loss.

31 Claims, 10 Drawing Sheets

(56) References Cited

OTHER PUBLICATIONS

Cohn et al. "Chain Extension as a Strategy for the Development of Improved Reverse Thermo-Responsive Polymers", Polymers for Advanced Technologies, 18: 731-736, 2007.

Cohn et al. "Improved Reverse Thermo-Responsive Polymeric Systems", Biomaterials, 24: 3707-3714, 2003.

Cohn et al. "Smart Hydrogels for In Situ Generated Implants", Biomacromolecules, 6: 1168-1175, 2005.

Dikovsky et al. "The Effect of Structural Alterations of PEG-Fibrogen Hydrogel Scaffolds on 3-D Cellular Morphology and Cellular Migration", Biomaterials, 27: 1496-1506, 2006.

Escobar-Chavez et al. "Applications of Thermo-Reversible Pluronic F-127 Gels in Pharmaceutical Formulations", Journal of Pharmacy and Pharmaceutical Sciences, 9(3): 339-358, 2006.

Frisman et al. "Nanostructuring PEG-Fibrinogen Hydrogels to Control Cellular Morphogenesis", Biomaterials, XP028268201, 32(31): 7839-7846, Available Online Jun. 30, 2011. 2. Experimental and 3.2 Increased Hydrogel Cross-Linking and Cell Morphology.

Nagarajan et al. "Comparison of Solubilization of Hydrocarbons in (PEO-PPO) Diblock Versus (PEO-PPO-PEO) Triblock Copolymer Micelles", Journal of Colloid and Interface Science, 184: 489-499, 1996.

Qiu et al. "Environment-Sensitive Hydrogels for Drug Delivery", Advanced Drug Delivery Reviews, 53: 321-339, 2001.

Sharma et al. "Effect of Anti-Inflammatories on Pluronic® F127: Micellar Assembly, Gelation and Partitioning", International Journal of Pharmaceutics, 278: 361-377, 2004.

Yom Tov "Characterization of PEG-Fibrinogen Nano-Structured Scaffolds for Tissue Engineering", Research Thesis, Submitted in Partial Fulfillment of the Requirements for the Degree of Master of Science in Chemical Engineering, Technion—Israel Institute of Technology, Haifa, IL, p. 1-97, Feb. 2011.

* cited by examiner

COMPOSITIONS COMPRISING A POLYMER-PROTEIN CONJUGATE AND AN ENVIRONMENTALLY-RESPONSIVE POLYMER AND USES THEREOF

RELATED APPLICATIONS

This application is a National Phase of PCT Patent Application No. PCT/IL2014/050575 having International filing date of Jun. 26, 2014, which claims the benefit of priority under 35 USC § 119(e) of U.S. Provisional Patent Application No. 61/839,951 filed on Jun. 27, 2013. The contents of the above applications are all incorporated by reference as if fully set forth herein in their entirety.

FIELD AND BACKGROUND OF THE INVENTION

The present invention, in some embodiments thereof, relates to environmentally-responsive compositions, and more particularly, but not exclusively, to compositions comprising a polymer-protein conjugate and an environmentally-responsive polymer, to scaffolds formed therefrom, and to uses thereof in, for example, tissue engineering.

Thermo-responsive polymers are capable of producing low viscosity aqueous solutions at low temperature, and forming a gel at a higher temperature, a property also referred to as "reverse thermal gelation". These polymers are therefore also referred to as "reverse thermo-responsive" polymers. Thermo-responsive polymers have been widely used in biomedical applications, such as the development of injectable and controlled drug delivery systems [Qiu & Park, *Adv Drug Deliv Rev* 2001, 53:321-339]. In addition, thermo-responsive polymers have been used in the development of in situ generated implants [Cohn et al., *Biomacromolecules* 2005, 6:1168-1175] or plugs [Bouchot et al., *Ann Thorac Surg* 2010, 89:1912-1917].

U.S. Patent Application Publication No. 2011/0052490 describes a use of compositions comprising a purified thermo-responsive polymer in an endoscopic procedure for gastrointestinal mucosal resectioning.

Thermo-responsive polymers having a poly(ethylene oxide) (PEO)-poly(propylene oxide) (PPO)-PEO tri-block structure, referred to as "poloxamers", have been reported to exhibit reverse thermal gelation. The endothermic sol-gel transition takes place due to an increase in entropy caused by release of water molecules bound to the PPO segments as temperature increases [Alexandridis, *Colloid Surface A* 1995, 96:1-46].

Pluronic® F127 poloxamer is a well known synthetic triblock copolymer ($PEO_{99}$-$PPO_{67}$-$PEO_{99}$) [Nagarajan and Ganesh, *J Colloid Interface Sci* 1996, 184:489-499; Sharma and Bhatia, Int J Pharm 2004, 278:361-377; Cohn et al., Biomaterials 2003, 24:3707-3714], that exhibits a reverse thermal gelation (RTG) property above a critical temperature in aqueous solutions. Pluronic® F127 poloxamer is approved for use in humans by the U.S. FDA and has been investigated for biomedical applications such as drug carrier for a variety of routes of administration, artificial skin, and as a barrier for treating post operative adhesions [Escobar-Chavez, *J Pharm Pharmaceut Sci* 2006, 9:339-358].

Additional thermo-responsive polymers which exhibit reverse thermal gelation include commercially available poly(N-isopropylacrylamide) (PNIPAAm) and poly(N,N-diethylacrylamide) (PDEAAm).

International Patent Application PCT/IL2004/001136 (published as WO 2005/061018) and U.S. Pat. No. 7,842, 667 disclose polymer-protein conjugates such as PEG (polyethylene glycol)-fibrinogen conjugates, and biodegradable scaffolds generated by cross-linking the conjugates, for example, by UV light. The scaffolds may be used for treating disorders requiring tissue regeneration.

PEG-fibrinogen hydrogels mimic the extracellular matrix (ECM), and contains necessary cell signaling domains within its amino acid sequence, including adhesion and protease degradation substrates, while the structural properties of the biosynthetic hydrogel network are controlled through the synthetic component [Dikovsky et al., *Biomaterials* 2006, 27:1496-1506].

International Patent Application PCT/IL2010/001072 (published as WO 2011/073991) discloses polymer-protein conjugates comprising a protein attached to at least two polymeric moieties, at least one of which exhibits reverse thermal gelation. The conjugates are suitable for being cross-linked by non-covalent and/or covalent cross-linking. The conjugates and compositions-of-matter formed by cross-linking the conjugates may be used for cell growth, tissue formation, and treatment of disorders characterized by tissue damage or loss.

Additional art includes Cohn et al. [*Polym Adv Tech* 2007; 18:731-736].

SUMMARY OF THE INVENTION

According to an aspect of some embodiments of the invention, there is provided a pharmaceutical, cosmetic or cosmeceutical composition comprising:

(a) a polymer-polypeptide conjugate comprising a polypeptide having attached thereto at least two polymeric moieties, wherein at least one of the polymeric moieties further comprises at least one polymerizable group, wherein molecules of the conjugate are not covalently linked to one another;

(b) a poloxamer;

(c) a poloxamer substituted by at least one polymerizable group; and (d) a pharmaceutically, cosmetically or cosmeceutically acceptable carrier, the composition exhibiting a reverse thermal gelation.

According to an aspect of some embodiments of the invention, there is provided a kit comprising a composition described herein.

According to an aspect of some embodiments of the invention, there is provided a composition-of-matter comprising a cross-linked form of a composition described herein, the cross-linked form comprising a plurality of molecules of the conjugate and the poloxamer substituted by at least one polymerizable group covalently cross-linked to one another upon polymerization of the polymerizable group.

According to an aspect of some embodiments of the invention, there is provided a process of producing a composition-of-matter described herein, the process comprising subjecting a composition described herein to conditions that effect covalent cross-linking by polymerization of the polymerizable group, thereby producing the composition-of-matter.

According to an aspect of some embodiments of the invention, there is provided a use of a composition or composition-of-matter described herein in the manufacture of a medicament for repairing tissue damage.

According to an aspect of some embodiments of the invention, there is provided a use of a composition or composition-of-matter described herein in the manufacture of a medicament for treating a subject having a disorder characterized by tissue damage or loss.

According to an aspect of some embodiments of the invention, there is provided a method of inducing formation of a tissue in vivo, the method comprising implanting a composition-of-matter described herein in a subject, to thereby induce the formation of the tissue.

According to an aspect of some embodiments of the invention, there is provided a method of inducing formation of a tissue in vivo, the method comprising administering a composition described herein to a subject, and subjecting the composition to conditions that effect covalent cross-linking by polymerization of the polymerizable group, to thereby induce the formation of the tissue.

According to an aspect of some embodiments of the invention, there is provided a method of treating a subject having a disorder characterized by tissue damage or loss, the method comprising implanting a composition-of-matter described herein in a subject, to thereby induce formation of the tissue, thereby treating the disorder characterized by tissue damage or loss.

According to an aspect of some embodiments of the invention, there is provided a method of treating a subject having a disorder characterized by tissue damage or loss, the method comprising administering to the subject a composition described herein, and subjecting the composition to conditions that effect covalent cross-linking by polymerization of the polymerizable group, to thereby induce formation of the tissue, thereby treating the disorder characterized by tissue damage or loss.

According to an aspect of some embodiments of the invention, there is provided a reverse thermal gelation composition characterized as:
  exhibiting a shear storage modulus of at least 100 Pa at temperatures in a range of from 17° C. to 21° C., and a shear storage modulus of less than 100 Pa at a temperature of 4° C.; and
  being curable in a physiological medium,
  for use in repairing damaged cartilage.

According to an aspect of some embodiments of the invention, there is provided a reverse thermal gelation composition characterized as:
  exhibiting a shear storage modulus of at least 100 Pa at temperatures in a range of from 17° C. to 21° C., and a shear storage modulus of less than 100 Pa at a temperature of 4° C.; and
  being curable in a physiological medium,
  for use in treating a subject having a disorder characterized by damage or loss of cartilage.

According to an aspect of some embodiments of the invention, there is provided a use of a reverse thermal gelation composition in the manufacture of a medicament for repairing damaged cartilage, the composition being characterized as:
  exhibiting a shear storage modulus of at least 100 Pa at temperatures in a range of from 17° C. to 21° C., and a shear storage modulus of less than 100 Pa at a temperature of 4° C.; and
  being curable in a physiological medium.

According to an aspect of some embodiments of the invention, there is provided a use of a reverse thermal gelation composition in the manufacture of a medicament for treating a subject having a disorder characterized by damage or loss of cartilage, the composition being characterized as:
  exhibiting a shear storage modulus of at least 100 Pa at temperatures in a range of from 17° C. to 21° C., and a shear storage modulus of less than 100 Pa at a temperature of 4° C.; and
  being curable in a physiological medium.

According to an aspect of some embodiments of the invention, there is provided a method of inducing formation of cartilage in vivo, the method comprising administering a reverse thermal gelation composition characterized as:
  exhibiting a shear storage modulus of at least 100 Pa at temperatures in a range of from 17° C. to 21° C., and a shear storage modulus of less than 100 Pa at a temperature of 4° C.; and
  being curable in a physiological medium,
  the method further comprising subjecting the composition in vivo to conditions that effect curing of the composition, to thereby induce the formation of cartilage.

According to an aspect of some embodiments of the invention, there is provided a method of treating a subject having a disorder characterized by damage or loss of cartilage, the method comprising administering a reverse thermal gelation composition characterized as:
  exhibiting a shear storage modulus of at least 100 Pa at temperatures in a range of from 17° C. to 21° C., and a shear storage modulus of less than 100 Pa at a temperature of 4° C.; and
  being curable in a physiological medium,
  the method further comprising subjecting the composition in vivo to conditions that effect curing of the composition, to thereby induce the formation of cartilage.

According to some embodiments of the invention, a shear storage modulus of the composition is at least 100 Pa at temperatures in a range of from 17° C. to 21° C., and less than 100 Pa at a temperature of 4° C.

According to some embodiments of the invention, the shear storage modulus is at least 1000 Pa at temperatures in a range of from 17° C. to 21° C.

According to some embodiments of the invention, the shear storage modulus is no more than 20000 Pa at temperatures in a range of from 17° C. to 21° C.

According to some embodiments of the invention, the shear storage modulus is less than 10 Pa at a temperature of 4° C.

According to some embodiments of the invention, the composition is characterized by a dissolution rate of less than 50 mg/cm$^2$ per hour in an aqueous environment.

According to some embodiments of the invention, a concentration of the conjugate in the composition is in a range of from 2 to 15 mg/ml.

According to some embodiments of the invention, a concentration of the poloxamer in the composition is in a range of from 13 to 25 weight percents.

According to some embodiments of the invention, a concentration of the poloxamer substituted by at least one polymerizable group in the composition is in a range of from 7.8 to 15 weight percents.

According to some embodiments of the invention, a total concentration of the poloxamer and the poloxamer substituted by at least one polymerizable group in the composition is at least 21 weight percents.

According to some embodiments of the invention, the conjugate has the general formula:

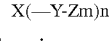

wherein:
X is the polypeptide;
Y is the polymeric moiety;

Z is the polymerizable group;

n is an integer greater than 1; and m is 1 or an integer greater than 1.

According to some embodiments of the invention, the polypeptide comprises a protein or a fragment thereof.

According to some embodiments of the invention, the protein is selected from the group consisting of an extracellular matrix protein, a cell signaling protein, a cell adhesion protein, a growth factor, protein A, a protease, and a protease substrate.

According to some embodiments of the invention, the protein is an extracellular matrix protein.

According to some embodiments of the invention, the extracellular matrix protein is selected from the group consisting of fibrinogen, collagen, fibronectin, elastin, fibrillin, fibulin, vimentin, laminin and gelatin.

According to some embodiments of the invention, the polypeptide comprises a fibrinogen or a fragment thereof.

According to some embodiments of the invention, the protein is a denatured protein.

According to some embodiments of the invention, the polypeptide is a denatured fibrinogen.

According to some embodiments of the invention, each of the polymeric moieties comprises a synthetic polymer.

According to some embodiments of the invention, the synthetic polymer is selected from the group consisting of a poly(ethylene glycol) and a poloxamer (poly(ethylene glycol-propylene glycol) copolymer).

According to some embodiments of the invention, the polymerizable group is polymerizable by free radical polymerization.

According to some embodiments of the invention, the polymerizable group is selected from the group consisting of an acrylate, a methacrylate, an acrylamide, a methacrylamide, and a vinyl sulfone.

According to some embodiments of the invention, the polypeptide is denaturated fibrinogen and each of the polymeric moieties comprises poly(ethylene glycol).

According to some embodiments of the invention, each of the poly(ethylene glycol) moieties comprises a poly(ethylene glycol) diacrylate moiety, wherein an acrylate group of the poly(ethylene glycol) diacrylate moiety is attached to a cysteine residue of the fibrinogen.

According to some embodiments of the invention, the polypeptide is denaturated fibrinogen and each of the polymeric moieties comprises F127 poloxamer.

According to some embodiments of the invention, each of the polymeric moieties comprises a F127 poloxamer diacrylate moiety, wherein an acrylate group of the F127 poloxamer diacrylate moiety is attached to a cysteine residue of the fibrinogen.

According to some embodiments of the invention, the composition further comprises a free radical initiator.

According to some embodiments of the invention, the reverse thermal gelation is characterized by a transition temperature in a range of from 10° C. to 20° C.

According to some embodiments of the invention, the reverse thermal gelation of the composition increases a shear storage modulus of the composition by at least ten-folds.

According to some embodiments of the invention, the composition is characterized by a shear storage modulus in a range of from 9,000 Pa to 15,000 Pa at a temperature of 17° C.

According to some embodiments of the invention, the composition is identified for use in generating a hydrogel scaffold.

According to some embodiments of the invention, the kit further comprises instructions for use in repairing tissue damage.

According to some embodiments of the invention, the kit further comprises instructions for use in treating a subject having a disorder characterized by tissue damage or loss.

According to some embodiments of the invention, the composition-of-matter is a scaffold.

According to some embodiments of the invention, the composition-of-matter is a hydrogel.

According to some embodiments of the invention, the composition-of-matter is characterized by a shear storage modulus of at least 30,000 Pa at a temperature of 17° C.

According to some embodiments of the invention, the composition-of-matter is biodegradable.

According to some embodiments of the invention, the composition-of-matter is identified for use in inducing a formation of a tissue.

According to some embodiments of the invention, the composition-of-matter is identified for use in repairing tissue damage.

According to some embodiments of the invention, the covalent cross-linking is effected in vivo.

According to some embodiments of the invention, the abovementioned conditions comprise irradiation.

According to some embodiments of the invention, the composition and/or composition-of-matter described herein is identified for use in repairing tissue damage.

According to some embodiments of the invention, the composition and/or composition-of-matter described herein is identified for use in treating a subject having a disorder characterized by tissue damage or loss.

According to some embodiments of the invention, the tissue comprises cartilage.

According to some embodiments of the invention, the composition is for use in arthroscopic surgery.

According to some embodiments of the invention, the medicament is for use in arthroscopic surgery.

According to some embodiments of the invention, the method is effected by arthroscopic surgery.

According to some embodiments of the invention, the composition is curable by polymerization in a physiological medium.

According to some embodiments of the invention, the polymerization in a physiological medium is initiated by irradiation.

According to some embodiments of the invention, the composition exhibits a reverse thermal gelation characterized by a transition temperature in a range of from 10° C. to 20° C.

According to some embodiments of the invention, the composition exhibits a reverse thermal gelation characterized by an increase in a shear storage modulus of the composition by at least ten-folds.

According to some embodiments of the invention, the composition forms a hydrogel scaffold upon curing in the physiological medium.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

(FIG. 2A) and stiffness at room temperature (FIG. 2B);

(FIG. 8A), removal of the mold after UV irradiation for 5 minutes at 4 mW/cm$^2$ (FIG. 8B), and the hydrogel formed by cross-linking the composition underwater (FIGS. 8B-8D);

DESCRIPTION OF SPECIFIC EMBODIMENTS OF THE INVENTION

Figure 1:
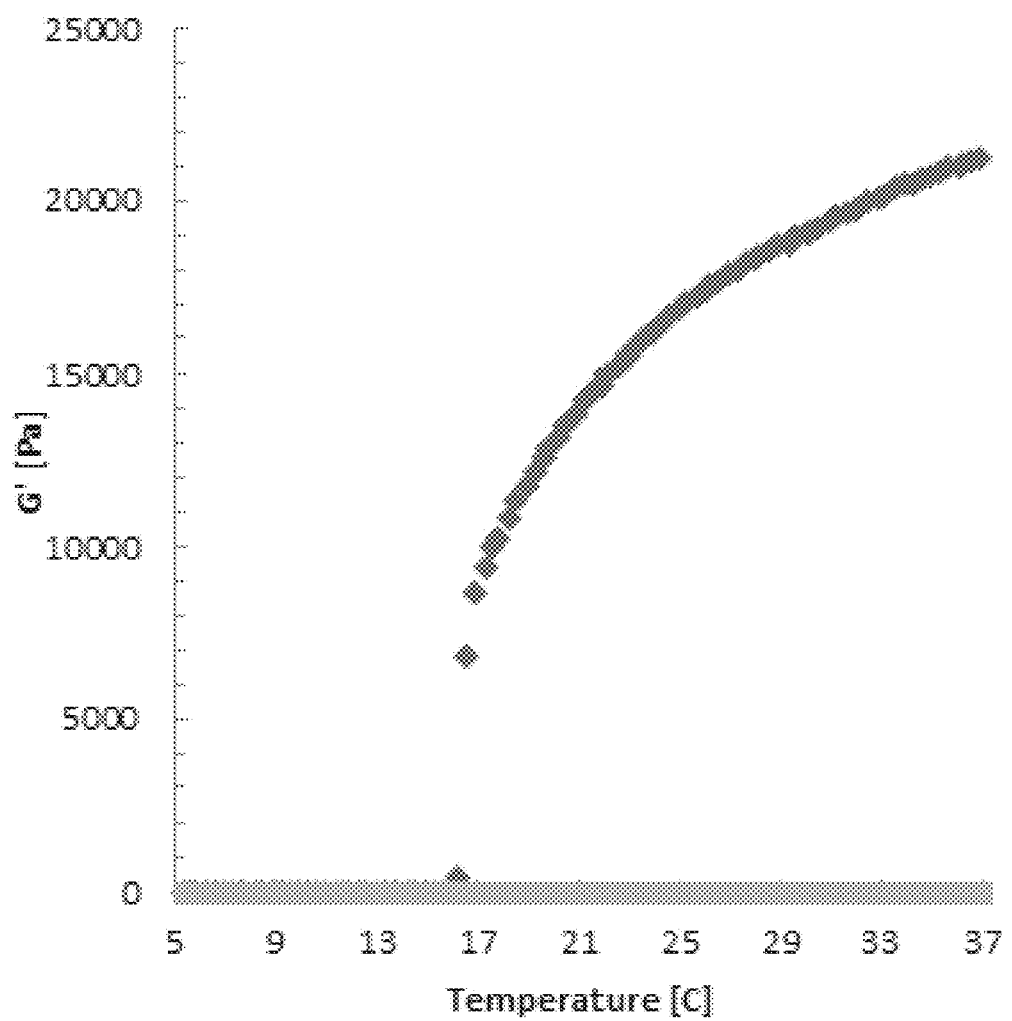
FIG. 1 is a graph showing the shear storage modulus (G') as a function of temperature for an exemplary composition comprising 7.3 mg/ml PEG-fibrinogen, 15.4% F127 poloxamer, and 8.1% F127 poloxamer-diacrylate (dark gray) and a composition comprising 7.4 mg/ml PEG-fibrinogen and 10% F127 poloxamer-diacrylate (light gray)

The present invention, in some embodiments thereof, relates to environmentally-responsive compositions, and more particularly, but not exclusively, to compositions comprising a polymer-protein conjugate and an environmentally-responsive polymer, to scaffolds formed therefrom, and to uses thereof in, for example, tissue engineering.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have designed and successfully prepared and practiced a composition which would exhibit properties which are highly suitable for forming a scaffold therefrom. While devising such a composition, the present inventors have considered that such a composition should exhibit the following general properties: relatively high fluidity at low temperatures, relatively high viscosity at room temperature, and an ability to be cross-linked in a physiological medium, such as in vivo. The present inventors have further considered the advantageous incorporation of a polypeptide (e.g., protein) within its structure. The present inventors have considered that such properties would allow for easy preparation and handling of a free-flowing liquid at low temperatures (e.g., upon refrigeration), while resulting in a composition which is sufficiently viscous at room temperature to remain in a desired location without spillage, while being sufficiently fluid so as to be injectable (e.g., via syringe). The composition, once in place, could then be cross-linked to form a desired material (e.g., a scaffold), which would comprise a polypeptide that provides advantageous biological signaling properties and/or biodegradability.

The present inventors have envisioned that polymers which exhibit reverse thermal gelation, such as poloxamers, may be useful for obtaining the desired viscosities at various temperatures. It is to be appreciated that in the composition designed and practiced by the present inventors, the reverse thermal gelation of such polymers is effected prior to injection, rather than being effected in situ.

Following laborious experimentation, the present inventors have devised a suitable composition, which combines at least the following components: a polymer-polypeptide conjugate comprising a polymerizable group which facilitates cross-linking; a poloxamer, which provides high viscosity at room temperature due to reverse thermal gelation properties; and a poloxamer substituted by at least one polymerizable group, which further facilitates both cross-linking and increase of viscosity at room temperature.

As demonstrated in the Examples section that follows, such a composition was shown to exhibit the desired rheological properties and pharmacological performance.

Hence, according to one aspect of embodiments of the invention, there is provided a reverse thermal gelation composition characterized as:

exhibiting a shear storage modulus of at least 100 Pa at temperatures in a range of from 17° C. to 21° C., and a shear storage modulus of less than 100 Pa at a temperature of 4° C.; and being curable in a physiological medium.

As used herein, the term "physiological medium" refers to water or an aqueous solution, characterized by a pH in a range of 5 to 9, and at a temperature in a range of from about 20° C. to about 37° C. In some embodiments, the physiological medium is a phosphate buffer saline (pH 7.4) solution, at a temperature of about 20° C.

As used herein, the term "curable" refers to an ability to undergo curing in response to a chemical and/or physical stimulus (e.g., illumination). When the term "curable" is associated with given conditions (e.g., "in a physiological medium"), the stimulus which effects curing must be compatible with the given conditions (e.g., not involve a pH or temperature incompatible with the definition of the conditions), as well as effect curing under said conditions.

Herein, the terms "curing" and "cure" and derivatives thereof refer to a hardening of a substance via formation of cross-links in response to a chemical and/or physical stimulus (e.g., illumination). In some embodiments, the hardening of a substance results in a shear storage modulus of the substance being at least 30,000 Pa at a temperature of 17° C.

It is expected that during the life of a patent maturing from this application many relevant polymers exhibiting reverse thermal gelation will be developed and the scope of the phrase "reverse thermal gelation composition" is intended to include compositions based on all such new technologies a priori.

A composition as described herein can be considered as environmentally-responsive composition since it exhibits changes in its properties (e.g., rheological properties, curability) which are responsive to environmental conditions (e.g., temperature, illumination, etc).

Herein throughout, the disclosed compositions are referred to interchangeably as "thermo-responsive compositions", "reverse thermal gelation compositions", and "environmentally-responsive compositions".

According to an aspect of embodiments of the invention, there is provided a pharmaceutical, cosmetic or cosmeceutical composition comprising:

a polymer-polypeptide conjugate comprising a polypeptide having attached thereto at least two polymeric moieties, wherein at least one of the polymeric moieties further comprises at least one polymerizable group, and wherein molecules of the conjugate are not covalently linked to one another;

a poloxamer;

a poloxamer substituted by at least one polymerizable group (also referred herein as a "polymerizable poloxamer", for the sake of brevity); and a pharmaceutically, cosmetically or cosmeceutically acceptable carrier, the composition exhibiting a reverse thermal gelation.

As exemplified herein, such a composition is susceptible to curing by causing molecules of conjugate (which are not covalently linked to one another) to become covalently linked by polymerization of polymerizable groups in the composition.

Such a composition can be considered as an environmentally-response composition, as defined herein.

Herein, the term "poloxamer" refers to a poly(ethylene oxide) (PEO)—poly(propylene oxide) (PPO) block copolymer having a PEO-PPO-PEO structure. Suitable poloxamers are commercially available, for example, as Pluronic® polymers. A "PEO" block is a moiety wherein ethylene oxide residues comprise at least 90% of the atoms of the moiety (excepting hydrogen atoms), and a "PPO" block is a moiety wherein propylene oxide residues comprise at least 90% of the atoms of the moiety (excepting hydrogen atoms).

Herein, wherever it is not indicated that a poloxamer is substituted by at least one polymerizable group, it is to be understood that poloxamers substituted by at least one polymerizable group are not encompassed by the term "poloxamer".

As used herein and in the art, the phrase "reverse thermal gelation" describes a property whereby a substance (e.g., a composition as described herein) increases in viscosity upon an increase in temperature. The increase in viscosity may be, for example, conversion from a liquid state to a semisolid state (e.g., gel), conversion from a liquid state to a more viscous liquid state, or conversion from a semisolid state to a more rigid semisolid state. Herein, all such conversions are encompassed by the term "gelation". The increase in temperature which effects gelation may be between any two temperatures. Optionally, the gelation is effected at a temperature within the range of 0° C. to 55° C.

For the sake of brevity, the term "thermo-responsive" refers herein to the property of exhibiting reverse thermal gelation (for both a composition and a substance).

As used herein and in the art, a "shear modulus" is defined as the ratio of shear stress to the shear strain. The shear modulus may be a complex variable, in which case the "shear storage modulus" (indicated by G') is the real component, and the "shear loss modulus" (indicated by G") is the imaginary component. The storage modulus and loss modulus in viscoelastic solids measure the stored energy, representing the elastic portion, and the energy dissipated as heat, representing the viscous portion.

In some embodiments, the reverse thermal gelation of the composition is such that the composition exhibits a shear storage modulus of at least 100 Pa at temperatures in a range of from 17° C. to 21° C. (i.e., at all temperatures within the aforementioned range), and a shear storage modulus of less than 100 Pa at the lower temperature of 4° C.

According to some embodiments of any of the aspects described herein, the shear storage modulus is at least 1000 Pa at temperatures in a range of from 17° C. to 21° C. In some embodiments, the shear storage modulus is at least 2000 Pa at temperatures in a range of from 17° C. to 21° C. In some embodiments, the shear storage modulus is at least 5000 Pa at temperatures in a range of from 17° C. to 21° C. In some embodiments, the shear storage modulus is at least 10000 Pa at temperatures in a range of from 17° C. to 21° C. In some embodiments, the shear storage modulus is about 12000 Pa at temperatures in a range of from 17° C. to 21° C.

In some embodiments, the shear storage modulus is no more than 20000 Pa at temperatures in a range of from 17° C. to 21° C. In some embodiments, the shear storage modulus is no more than 15000 Pa at temperatures in a range of from 17° C. to 21° C.

According to some embodiments of any of the aspects described herein, the shear storage modulus is in a range of from 9,000 Pa to 15,000 Pa at a temperature of 17° C. In some embodiments, the shear storage modulus is in a range of from 10,000 Pa to 13,000 Pa at a temperature of 17° C. In some embodiments, the shear storage modulus is about 12,000 Pa at a temperature of 17° C.

In some embodiments, the shear storage modulus is less than 10 Pa at a temperature of 4° C. In some embodiments, the shear storage modulus is less than 5 Pa at a temperature of 4° C. In some embodiments, the shear storage modulus is less than 2 Pa at a temperature of 4° C. In some embodiments, the shear storage modulus is less than 1 Pa at a temperature of 4° C. In some embodiments, the shear storage modulus is less than 0.5 Pa at a temperature of 4° C. In some embodiments, the shear storage modulus is less than 0.2 Pa at a temperature of 4° C.

Low viscosity liquids are particularly advantageous in the manufacturing stage of compositions such as described herein, as the they readily allow mixing of ingredients, as well as purification and sterilization steps such as filtration.

Without being bound by any particular theory, it is believed that compositions which have a low viscosity state at moderately low temperatures are advantageous in that they require only a moderate degree of cooling (e.g., thereby saving energy) in order to benefit from the abovementioned advantages of the low viscosity state.

In some embodiments of any of the aspects described herein, the reverse thermal gelation is characterized by a transition temperature (wherein the composition is in a more viscous state at temperatures above the transition temperature) in a range of from 10° C. to 20° C. In some embodiments, the reverse thermal gelation is characterized by a transition temperature in a range of from 13° C. to 19° C. In some embodiments, the reverse thermal gelation is characterized by a transition temperature in a range of from 15° C. to 18° C.

The transition temperature may be determined, using procedures known in the art, by identifying a temperature at which the composition undergoes a sudden change in properties, for example, a sudden change in shear storage modulus and/or a phase transition as determined using calorimetry.

In some embodiments of any of the aspects described herein, the reverse thermal transition of the composition increase a shear storage modulus of the composition by at least 10-folds. In some embodiments, the reverse thermal transition of the composition increases a shear storage modulus of the composition by at least 30-folds. In some embodiments, the reverse thermal transition of the composition increases a shear storage modulus of the composition by at least 100-folds. In some embodiments, the reverse thermal transition of the composition increases a shear storage modulus of the composition by at least 300-folds. In some embodiments, the reverse thermal transition of the composition increases a shear storage modulus of the composition by at least 1,000-folds. In some embodiments, the reverse thermal transition of the composition increases a shear storage modulus of the composition by at least 3,000-folds. In some embodiments, the reverse thermal transition of the composition increases a shear storage modulus of the composition by at least 10,000-folds.

As exemplified herein, exemplary compositions retain their advantageous rheological and curing properties even after being incubated in water.

Without being bound by any particular theory, it is believed that such a property enhances the usefulness of compositions described herein for applications in an aqueous environment, including in vivo environments.

Hence, according to some embodiments of any of the aspects described herein, the composition is water-resistant.

Herein, the term "water-resistant" refers to a substance (e.g., a composition described herein) which, upon its incubation in water for at least an hour, no appreciable uptake of water is made by the substance and no appreciable uptake of the substance or a portion thereof is made by the water. The substance thus retains an identifiable and relatively stationary boundary with the adjacent water, which may be rendered highly visible by adding a water-soluble dye to the water or substance, as exemplified herein.

Herein, the phrase "appreciable uptake" refers to a net movement of molecules from one substance to another (e.g., from a composition described herein to water, or vice versa) at a degree of at least 500 mg/cm$^2$.

In some embodiments, the water-resistance is such that the composition is characterized by a dissolution rate of less than 100 mg/cm$^2$ per hour in an aqueous environment.

As defined herein, the "dissolution rate" is determined by contacting the composition with an aqueous solution (e.g., phosphate buffer saline pH 7.4) for one hour in the absence of stirring, for example, by gently placing the aqueous solution above the composition, and determining an amount of dissolution of the composition (as determined by a decrease in the weight of the composition) at a temperature of 20° C. In some embodiments, the dissolution rate is less than 50 mg/cm$^2$ per hour. In some embodiments, the change in weight is less than 40 mg/cm$^2$ per hour. In some embodiments, the change in weight is less than 30 mg/cm$^2$ per hour.

The change in weight in units of mg/cm$^2$ may be determined by measuring a change in weight of a composition in a sample, and dividing the change in weight by an area of the interface between the composition and the aqueous solution. As exemplified herein, such a test may be performed using about 1 ml of each of the composition and aqueous solution, with an interface between the composition and water is about 38 mm$^2$.

The term "water-resistant" encompasses both water-immiscible substances, as well as substances which are miscible with water when sufficiently stirred, but which resist water (e.g., dissolve very slowly in the water) in the absence of sufficient stirring.

The Polymer-Polypeptide Conjugate:

The polymer-polypeptide conjugate according to any one of the embodiments described in this section may be used in the context of any one of the embodiments of any of the aspects of the inventions described herein, and may be combined with a poloxamer according to any one of the respective embodiments described herein and with a polymerizable poloxamer according to any one of the respective embodiments described herein.

In some embodiments of any one of the embodiments described herein, a concentration of the polymer-polypeptide (or polymer-protein) conjugate in the composition is in a range of from 2 to 15 mg/ml. In some embodiments, a concentration of the conjugate is in a range of from 5 to 10 mg/ml. In some embodiments, a concentration of the conjugate is in a range of from 6 to 9 mg/ml. In some embodiments, a concentration of the conjugate is about 7.3 mg/ml.

In some embodiments of any one of the embodiments described herein, a concentration of the conjugate in the composition is in a range of from 2 to 8 mg/ml. In some embodiments, a concentration of the conjugate is in a range of from 5 to 8 mg/ml. In some embodiments, a concentration of the conjugate is in a range of from 6 to 8 mg/ml.

In some embodiments of any one of the embodiments described herein, a concentration of the conjugate in the composition is in a range of from 6 to 15 mg/ml. In some embodiments, a concentration of the conjugate is in a range of from 6 to 10 mg/ml. In some embodiments, a concentration of the conjugate is in a range of from 6 to 9 mg/ml.

In some embodiments of any one of the embodiments described herein, the conjugate has the general formula:

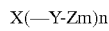

wherein X is a polypeptide as described herein, Y is a polymeric moiety as described herein, Z is a polymerizable group as described herein, n is an integer greater than 1 (e.g., 2, 3, 4 and up to 20), and m is 1 or an integer greater than 1 (e.g., 2, 3, 4 and up to 20) which represents the number of polymerizable groups per polymeric moiety.

In some embodiments of any one of the embodiments described herein, m is in a range of from 1 to 10. In some embodiments, m is in a range of from 1 to 4. In some embodiments, m is 1.

It is to be understood that as the above formula includes more than one —Y-Zm moiety, different —Y-Zm moieties in a conjugate may optionally have a different values for m.

In some embodiments of any one of the embodiments described herein, the polymeric moieties comprise a synthetic polymer. Poloxamers (e.g., F127 poloxamer) and poly(ethylene glycol) are exemplary synthetic polymers suitable for polymeric moieties according to embodiments of the present invention.

Without being bound by any particular theory, it is believed that conjugation of a synthetic polymer to a polypeptide (e.g., a natural protein such as fibrinogen) provides a means of creating biocompatible hydrogels while controlling their physical properties (e.g., density, stiffness, and proteolytic degradability) through the versatile synthetic component, without compromising biocompatibility.

The polypeptide of the conjugate is at least 10 amino acids in length, optionally at least 20 amino acids in length, and optionally at least 50 amino acids in length.

The term "polypeptide" as used herein encompasses native polypeptides (either degradation products, synthetically synthesized polypeptides or recombinant polypeptides) and peptidomimetics (typically, synthetically synthesized polypeptides), as well as peptoids and semipeptoids which are polypeptide analogs, which may have, for example, modifications rendering the polypeptides more stable while in a body or more capable of penetrating into cells. Such modifications include, but are not limited to, N-terminus modification, C-terminus modification, peptide bond modification, including, but not limited to, $CH_2$—NH, $CH_2$—S, $CH_2$—S=O, O=C—NH, $CH_2$—O, $CH_2$—$CH_2$, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the polypeptide may be substituted, for example, by N-methylated bonds (—N($CH_3$)—CO—), ester bonds (—C(R)H—C—O—O—C(R)—N—), ketomethylene bonds (—CO—$CH_2$—), α-aza bonds (—NH—N(R)—CO—), wherein R is any alkyl, e.g., methyl, amine bonds (—$CH_2$—NH—), hydroxyethylene bonds (—CH(OH)—$CH_2$—), thioamide bonds (—CS—NH—), olefinic double bonds (—CH=CH—), retro amide bonds (—NH—CO—), peptide derivatives (—N(R)—$CH_2$—CO—), wherein R is the "normal" side chain, naturally presented on the carbon atom. These modifications can occur at any of the bonds along the polypeptide chain and even at several (2-3) at the same time.

As used herein throughout, the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

According to some embodiments of any one of the embodiments described herein, the polypeptide comprises a protein or a fragment thereof.

In some embodiments, the terms "polypeptide" and "protein" are used interchangeably.

The protein may be a naturally occurring protein (e.g., a protein existing in eukaryotic and/or prokaryotic organisms, cells, cellular material, non-cellular material, and the like) or a polypeptide homologous (e.g., at least 90% homologous, optionally at least 95% homologous, and optionally at least 99% homologous) to a naturally occurring protein.

In some embodiments of any one of the embodiments described herein, the protein (or protein fragment) is denatured.

It is to be understood that the protein described herein may optionally comprise more than one polypeptide chain.

In embodiments comprising a protein characterized by more than one polypeptide chain, the conjugate described herein optionally comprises one polypeptide of the protein.

Alternatively, the conjugate described herein comprises a plurality of polypeptides of the protein (e.g., all of the polypeptides of the protein). In some embodiments of any one of the embodiments described herein, the plurality of polypeptides are linked together (e.g., by non-covalent and/or covalent bonds) so as to form a multimer (e.g., a dimer, a trimer, a tetramer, a hexamer, etc.), the multimer having attached thereto at least two polymeric moieties, as described herein. In some embodiments, the polypeptides of the protein are separate (e.g., separated by denaturation of the protein), such that the conjugate described herein is a mixture of different conjugate species, wherein each of the conjugate species comprises a different polypeptide.

In some embodiments of any one of the embodiments described herein, the polypeptide (e.g., protein or protein fragment) is selected so as to exhibit a biological activity. In some embodiments, the biological activity comprises support for cell growth and/or invasion.

Examples of proteins exhibiting a biological activity which is advantageous in the context of embodiments of the present invention include, without limitation, a cell signaling protein, an extracellular matrix protein, a cell adhesion protein, a growth factor, protein A, a protease and a protease substrate. In some embodiments of any one of the embodiments described herein, the protein is an extracellular matrix protein.

According to some embodiments of any one of the embodiments described herein, the polypeptide comprises a fibrinogen polypeptide (α, β and/or γ chains of fibrinogen) or a fragment thereof. In some embodiments, the conjugate described herein comprises the α, β and γ chains of fibrinogen. In some embodiments, the polypeptide is a denatured fibrinogen (e.g., a mixture of denatured α, β and γ chains of fibrinogen).

Examples of extracellular matrix proteins include, but are not limited to, fibrinogen (e.g., α-chain—GenBank Accession No. NP_068657; β-chain—GenBank Accession No. P02675; γ-chain—GenBank Accession No. P02679), collagen (e.g., GenBank Accession No. NP_000079), fibronectin (e.g., GenBank Accession No. NP_002017), vimentin (e.g., GenBank Accession No. NP_003371), elastin, fibrillin, fibulin, laminin (e.g., GenBank Accession No. NP_000218) and gelatin.

Examples of cell signaling proteins include, but are not limited to, p38 mitogen-activated protein kinase (e.g., GenBank Accession No. NP_002736), nuclear factor kappaB (e.g., GenBank Accession No. NP_003989), Raf kinase inhibitor protein (RKIP) (e.g., GenBank Accession No. XP_497846), Raf-1 (e.g., GenBank Accession No. NP_002871), MEK (e.g., GenBank Accession No. NP_002746), protein kinase C (PKC) (e.g., GenBank Accession No. NP_002728), phosphoinositide-3-kinase gamma (e.g., GenBank Accession No. NP_002640), receptor tyrosine kinases such as insulin receptor (e.g., GenBank Accession No. NP_000199), heterotrimeric G-proteins (e.g., Galpha(i)—GenBank Accession No. NP_002060; Galpha(s)—GenBank Accession No. NP_000507; Galpha(q)—GenBank Accession No. NP_002063), caveolin-3 (e.g., GenBank Accession No. NP_001225), microtubule associated protein 1B, and 14-3-3 proteins (e.g., GenBank Accession No. NP_003397).

Examples of cell adhesion proteins include, but are not limited to, integrin (e.g., GenBank Accession No. NP_002202), intercellular adhesion molecule (ICAM) 1 (e.g., GenBank Accession No. NP_000192), N-CAM (e.g., GenBank Accession No. NP_000606), cadherin (e.g., GenBank Accession No. NP_004351), tenascin (e.g., GenBank Accession No. NP_061978), gicerin (e.g., GenBank Accession No. NP_006491), and nerve injury induced protein 2 (ninjurin2) (e.g., GenBank Accession No. NP_067606).

Examples of growth factors include, but are not limited to, epidermal growth factor (e.g., GenBank Accession No. NP_001954), transforming growth factor-β (e.g., GenBank Accession No. NP_000651), fibroblast growth factor-acidic (e.g., GenBank Accession No. NP_000791), fibroblast growth factor-basic (e.g., GenBank Accession No. NP_001997), erythropoietin (e.g., GenBank Accession No. NP_000790), thrombopoietin (e.g., GenBank Accession No. NP_000451), neurite outgrowth factor, hepatocyte growth factor (e.g., GenBank Accession No. NP_000592), insulin-like growth factor-I (e.g., GenBank Accession No. NP_000609), insulin-like growth factor-II (e.g., GenBank Accession No. NP_000603), interferon-γ (e.g., GenBank Accession No. NP_000610), and platelet-derived growth factor (e.g., GenBank Accession No. NP_079484).

Examples of proteases include, but are not limited to, pepsin (e.g., GenBank Accession No. NP_055039), low specificity chymotrypsin, high specificity chymotrypsin, trypsin (e.g., GenBank Accession No. NP_002760), carboxypeptidases (e.g., GenBank Accession No. NP_001859), aminopeptidases (e.g., GenBank Accession No. NP_001141), proline-endopeptidase (e.g. GenBank Accession No. NP_002717), Staphylococcus aureus V8 protease (e.g., GenBank Accession No. NP_374168), proteinase K (PK) (e.g., GenBank Accession No. P06873), aspartic protease (e.g., GenBank Accession No. NP_004842), serine proteases (e.g., GenBank Accession No. NP_624302), metalloproteases (e.g., GenBank Accession No. NP_787047), ADAMTS17 (e.g., GenBank Accession No. NP_620688), tryptase-γ (e.g., GenBank Accession No. NP_036599), matriptase-2 (e.g., GenBank Accession No. NP_694564).

Examples of protease substrates include the peptide or peptide sequences being the target of the protease protein. For example, lysine and arginine are the target for trypsin; tyrosine, phenylalanine and tryptophan are the target for chymotrypsin.

Such naturally occurring proteins can be obtained from any known supplier of molecular biology reagents.

According to some embodiments of any one of the embodiments described herein, the polymeric moieties of the conjugate comprise polymerizable groups (e.g., as described herein) which can attach to a polypeptide. For example, acrylate, methacrylate, acrylamide, methacrylamide, and vinyl sulfone, in addition to being polymerizable groups, are suitable for attachment to a thiol group (e.g., in a cysteine residue) via Michael-type addition.

Thus, as exemplified in the Examples section herein, a polymeric moiety may comprise a plurality of such groups (e.g., acrylate), one of which reacted (which may render the group no longer polymerizable) so as to attach the polymeric moiety to the polypeptide, the remaining group or groups being polymerizable groups.

In some embodiments of any one of the embodiments described herein, the conjugate comprises polymer diacrylate (e.g., poly(ethylene glycol) diacrylate) moieties, wherein one acrylate group in each moiety is attached to a cysteine residue of a polypeptide (e.g., denatured fibrinogen), and one acrylate group serves as a polymerizable group.

In some embodiments of any one of the embodiments described herein, the conjugate comprises a branched polymeric moiety substituted by more than two acrylate groups (e.g., 4-armed poly(ethylene glycol) tetraacrylate moieties), wherein one acrylate group in each moiety is attached to a cysteine residue of a polypeptide (e.g., denatured fibrinogen), and the other acrylate groups (e.g., three acrylate groups in a tetraacrylate moiety) serve as polymerizable groups.

According to some embodiments, the polypeptide is denatured fibrinogen and each of the polymeric moieties comprises poly(ethylene glycol).

According to some embodiments of any one of the embodiments described herein, each of the poly(ethylene glycol) moieties comprises a poly(ethylene glycol) diacrylate moiety, wherein an acrylate group of the poly(ethylene glycol) diacrylate moiety is attached to a cysteine residue of the fibrinogen.

According to some embodiments of any one of the embodiments described herein, the polypeptide is denatured fibrinogen and each of the polymeric moieties comprises F127 poloxamer.

According to some embodiments of any one of the embodiments described herein, each of the polymeric moieties comprises an F127 poloxamer diacrylate moiety, wherein an acrylate group of the F127 poloxamer diacrylate moiety is attached to a cysteine residue of the fibrinogen.

Polymer-polypeptide conjugates suitable for use in embodiments of the invention are also described in International Patent Application Publication WO 2005/061018, U.S. Pat. No. 7,842,667 and International Patent Application Publication WO 2011/073991, the contents of which are incorporated herein by reference.

The Polymerizable Groups and Polymerization:

The polymerizable groups and polymerization according to any one of the embodiments described in this section may be used in the context of any one of the embodiments of any of the aspects of the inventions described herein, and may be incorporated within a polymerizable polymer-polypeptide conjugate according to any one of the respective embodiments described herein and within a polymerizable poloxamer according to any one of the respective embodiments described herein.

As used herein, the phrase "polymerizable group" refers to a functional group characterized by an ability to effect covalent cross-linking by polymerization of the polymerizable group with a functional group of another molecule (e.g., another conjugate). In the context of any embodiments of the present invention, the polymerizable groups may act as monomers, whereby polymerization of the polymerizable groups cross-links the conjugates comprising the polymerizable groups.

According to some embodiments of any one of the embodiments described herein, the polymerizable group is able to effect cross-linking via polymerization with a molecule (e.g., polymer-protein conjugate, substituted poloxamer) similar to and/or identical to a polymerizable-group-containing molecule described herein (e.g., a conjugate or poloxamer comprising a polymerizable group chemically related to and/or identical to the polymerizable group described herein).

Herein, the term "polymerization" refers to a reaction in which at least two chemically similar or identical molecules or moieties become covalently linked by one or more bonds. The reaction and the bonds formed thereby are of a type which allows, at least under some conditions, for more than two (e.g., 10 or more) of the chemically similar or identical molecules or moieties to become covalently linked.

Many polymerizable groups are known in the art, including groups (e.g., unsaturated groups) which readily undergo free radical polymerization, and cyclic groups (e.g., lactones) which readily undergo polymerization via ring-opening.

Various conditions for effecting polymerization (e.g., free radical polymerization) are known in the art. Polymerization can be effected, for example, via photoinitiation (in the presence of irradiation with appropriate light, e.g., 365 nm, and optionally also an initiator as described herein), via chemical cross-linking (in the presence of a free-radical donor) and/or heating (at the appropriate temperatures). According to exemplary embodiments, polymerization is effected by irradiation with UV light (e.g., at a wavelength of about 365 nm).

In some embodiments of any one of the embodiments described herein, a polymerizable group is selected such that polymerization thereof may be effected under relatively mild conditions which are non-harmful to living cells. For example, the polymerization conditions are optionally sufficiently non-toxic and non-hazardous so as to be suitable for effecting polymerization in vivo, as described herein.

In some embodiments of any one of the embodiments described herein, the polymerizable group is polymerizable by free radical polymerization. Examples of such groups include, without limitation, an acrylate, a methacrylate, an acrylamide, a methacrylamide, and a vinyl sulfone.

In any of the aspects of embodiments of the invention, a free radical initiator may optionally be used in order to initiate polymerization of the polymerizable groups described herein. The skilled person will be capable of selecting an initiator suitable for initiating polymerization of the selected polymerizable group(s).

In some embodiments of any one of the embodiments described herein, a composition as described herein further comprises a free radical initiator (e.g., as described herein).

The Poloxamer and Poloxamer Substituted by at Least One Polymerizable Group:

The poloxamer and poloxamer substituted by at least one polymerizable group according to any one of the embodiments described in this section may be used in the context of any one of the embodiments of any of the aspects of the inventions described herein, and may be combined with a conjugate according to any one of the respective embodiments described herein, and may comprise a polymerizable group according to any one of the respective embodiments described herein.

In some embodiments of any one of the embodiments described herein, a concentration of the poloxamer is at least 5 weight percents. In some embodiments, a concentration of the poloxamer is at least 8 weight percents. In some embodiments, a concentration of the poloxamer is at least 10 weight percents. In some embodiments, a concentration of the poloxamer is at least 12 weight percents.

In some embodiments of any one of the embodiments described herein, a concentration of the poloxamer is in a range of from 13 to 25 weight percents. In some embodiments, a concentration of the poloxamer is in a range of from 13 to 20 weight percents. In some embodiments, a concentration of the poloxamer is in a range of from 13.5 to 17.5 weight percents. In some embodiments, a concentration of the poloxamer is about 15.4 weight percents.

F127 poloxamer is an exemplary poloxamer, which may optionally be used in some embodiments of any one of the embodiments described herein.

In some embodiments of any one of the embodiments described herein, a concentration of the poloxamer substituted by at least one polymerizable group is at least 3 weight percents. In some embodiments, a concentration of the poloxamer substituted by at least one polymerizable group is at least 5 weight percents. In some embodiments, a concentration of the poloxamer substituted by at least one polymerizable group is at least 7 weight percents.

In some embodiments of any one of the embodiments described herein, a concentration of the poloxamer substituted by at least one polymerizable group is in a range of from 7.8 to 15 weight percents. In some embodiments, a concentration of the poloxamer substituted by at least one polymerizable group is in a range of from 7.8 to 12 weight percents. In some embodiments, a concentration of the poloxamer substituted by at least one polymerizable group is in a range of from 7.8 to 10 weight percents.

In some embodiments of any one of the embodiments described herein, a concentration of the poloxamer substituted by at least one polymerizable group is about 8.1 weight percents.

In some embodiments of any one of the embodiments described herein, a total concentration of the poloxamer and the poloxamer substituted by at least one polymerizable group is at least 19 weight percents. In some embodiments, the total concentration is at least 21 weight percents. In some embodiments, the total concentration is at least 22 weight percents.

In some embodiments of any one of the embodiments described herein, a total concentration of the poloxamer and the poloxamer substituted by at least one polymerizable group is no more than 30 weight percents. In some embodiments, the total concentration is no more than 27 weight percents. In some embodiments, the total concentration is no more than 25 weight percents.

In some embodiments of any one of the embodiments described herein, a total concentration of the poloxamer and the poloxamer substituted by at least one polymerizable group is about 23.5 weight percents.

In some embodiments of any one of the embodiments described herein, the substituted poloxamer is an F127 poloxamer substituted by at least one polymerizable group.

In some embodiments of any one of the embodiments described herein, the substituted poloxamer is substituted with at least two polymerizable groups (e.g., acrylate) described herein, for example, 2, 3, 4 and up to 20 polymerizable groups. In some embodiments, the substituted poloxamer comprises two polymerizable groups described herein, for example, the substituted poloxamer is a poloxamer diacrylate. F127 poloxamer diacrylate is an exemplary poloxamer diacrylate which may optionally be used in some embodiments of any one of the embodiments described herein.

The Composition-of-Matter in Cross-Linked Form:

The composition-of-matter according to any one of the embodiments described in this section may be used in the context of any one of the embodiments of any of the aspects of the inventions described herein, and may be comprise a conjugate according to any one of the respective embodiments described herein, a poloxamer according to any one of the respective embodiments described herein, and a polymerizable poloxamer according to any one of the respective embodiments described herein. In addition, the cross-linking may be effected by a polymerizable group according to any one of the respective embodiments described herein.

According to another aspect of embodiments of the invention, there is provided a cross-linked form of any of the compositions comprising a polymer-polypeptide conjugate, as described herein. The cross-linked form comprises a plurality of molecules of the conjugate (as described herein) and a plurality of molecules of a poloxamer substituted by at least one polymerizable group (as described herein) covalently cross-linked to one another upon polymerization of the polymerizable group (e.g., as described herein).

In some embodiments of any one of the embodiments described herein, the composition-of-matter is a scaffold.

As used herein, the term "scaffold" describes a two-dimensional or a three-dimensional supporting framework. The scaffold according to embodiments of the present invention is composed of precursor units (comprising the conjugates and/or poloxamer substituted by at least one polymerizable group, as described herein) which are cross-linked therebetween. The scaffold may further comprise compounds (such as the poloxamer described herein) which are contained within the scaffold, without being cross-linked to the aforementioned precursor units.

In some embodiments of any one of the embodiments described herein, a scaffold can be used as a support for cell growth, attachment and/or spreading and thus facilitates tissue generation and/or tissue repair. In some embodiments, a scaffold maintains a desired shape of a tissue and/or cell colony supported thereby.

It is to be understood that a "cross-linked form" of a composition as described herein may comprise a lower proportion of poloxamer (as described herein) than the composition per se, because the poloxamer generally does not undergo covalent cross-linking (in contrast to the conjugate and poloxamer substituted by at least one polymerizable group, as described herein), and therefore may leak out of the cross-linked form.

In some embodiments of any one of the embodiments described herein, the composition-of-matter is a hydrogel.

As used herein and is well-known in the art, the term "hydrogel" refers to a material that comprises solid networks (e.g., a scaffold described herein) formed of water-soluble natural and/or synthetic polymer chains, which may contain substantial amounts (e.g., more than 99%) of water.

The hydrogel may be a cross-linked form of a composition described herein per se, that is, the water contained in of the hydrogel is substantially the same as the water in the composition prior to cross-linking.

Alternatively, the hydrogel may comprise water absorbed by the composition-of-matter subsequent to cross-linking of a composition described herein.

Without being bound by any particular theory, it is believed that hydrogels at are particularly advantageous for applications such as tissue regeneration, as they provide a desirable solid or semi-solid consistency while containing a considerable degree of aqueous environment which is suitable for allowing cell growth and migration within the hydrogel.

In some embodiments of any one of the embodiments described herein, the composition-of-matter is characterized by a shear storage modulus of at least 30,000 Pa at a temperature of 17° C. In some embodiments, the shear storage modulus is at least 35,000 Pa at a temperature of 17° C. In some embodiments, the shear storage modulus is at least 40,000 Pa at a temperature of 17° C. In some embodiments, the shear storage modulus is about 45,000 Pa a temperature of 17° C.

In some embodiments of any one of the embodiments described herein, the composition-of-matter is biodegradable, i.e., the composition-of-matter degrades upon contact with a tissue and/or a cell (e.g., by proteolysis and/or hydrolysis). Biodegradable materials are useful in various medical applications, for example as temporary implants. In addition, biodegradable materials are highly suitable as matrices for supporting cell growth and/or migration, as cell growth and/or migration is associated with degradation of a surrounding matrix.

In some embodiments of any one of the embodiments described herein, biodegradability of a composition-of-matter is a result of the biodegradability of a polypeptide of a conjugate (as described herein) within the composition-of-matter, such that degradation of the polypeptide causes degradation of the composition-of-matter.

According to another aspect of embodiments of the invention, there is provided a process for producing a composition-of-matter described herein, the process comprising subjecting a composition described herein to conditions that effect covalent cross-linking by polymerization of the polymerizable group, as described herein.

In some embodiments of any one of the embodiments described herein, the covalent cross-linking is effected in vivo.

In some embodiments of any one of the embodiments described herein, the covalent cross-linking is effected ex vivo.

In some embodiments of any one of the embodiments described herein, conditions that effect covalent cross-linking by polymerization comprise irradiation (e.g., as described herein).

Applications of the Composition and Composition-of-Matter:

The applications according to any one of the embodiments described in this section may be performed in the context of any one of the embodiments of any of the aspects of the inventions described herein, and may utilize a composition according to any one of the respective embodiments described herein and/or a composition-of-matter according to any one of the respective embodiments described herein.

According to some embodiments of any one of the embodiments of any of the aspects described herein, any of the compositions as described herein is identified for use in generating a hydrogel scaffold (e.g., as described herein).

According to some embodiments of any one of the embodiments of any of the aspects described herein, any of the compositions as described herein and/or any of the compositions-of-matter as described herein is identified for use in repairing damaged tissue.

According to some embodiments of any one of the embodiments of any of the aspects described herein, any of the compositions as described herein and/or any of the compositions-of-matter as described herein is identified for use in treating a subject having a disorder characterized by tissue damage or loss.

According to some embodiments of any one of the embodiments of any of the aspects described herein, any of the compositions as described herein and/or any of the compositions-of-matter as described herein is identified for use in inducing formation of a tissue.

According to another aspect of embodiments of the invention, there is provided a use of any of the compositions as described herein and/or any of the compositions-of-matter as described herein in the manufacture of a medicament for repairing tissue damage.

According to another aspect of embodiments of the invention, there is provided a use of any of the compositions as described herein and/or any of the compositions-of-matter as described herein in the manufacture of a medicament for treating a subject having a disorder characterized by tissue damage or loss.

According to another aspect of embodiments of the invention, there is provided a method of inducing formation of a tissue in vivo, the method comprising administering any of the compositions as described herein to a subject.

According to another aspect of embodiments of the invention, there is provided a method of treating a subject having a disorder characterized by tissue damage or loss, the method comprising administering any of the compositions as described herein to the subject.

Any of the methods and uses which utilize a composition as described herein (e.g., for repairing repair tissue damage, for manufacturing a medicament, for treating a subject and/or for inducing formation of a tissue) may be effected by subjecting the composition (e.g., in vivo) to conditions that effect curing of the composition, as described herein, to thereby induce formation of tissue. In some embodiments of any one of the embodiments described herein, curing is effected by covalent cross-linking.

In some embodiments, covalent cross-linking is effected by polymerization of the polymerizable group, as described herein.

According to another aspect of embodiments of the invention, there is provided a method of inducing formation of a tissue in vivo, the method comprising implanting any of the compositions-of-matter as described herein in a subject, to thereby induce the formation of tissue.

According to another aspect of embodiments of the invention, there is provided a method of treating a subject having a disorder characterized by tissue damage or loss, the method comprising implanting any of the compositions-of-matter as described herein in the subject, to thereby induce the formation tissue.

In some embodiments of any one of the embodiments of any of the methods and uses which utilize composition-of-matter as described herein (e.g., by implanting the composition-of-matter and/or for manufacturing a medicament), the composition-of-matter is prepared in a shape suitable for a subject in which the composition-of-matter is to be implanted, as determined, for example, by a treating physician (e.g., a surgeon). In some embodiments, the composition-of-matter is prepared in the desired shape by preparing a mold in the desired shape, and subjecting a composition described herein to covalent cross-linking in the mold (e.g., as described herein).

In some embodiments of any one of the embodiments of any of the aspects described herein, the tissue comprises cartilage, and the composition is for use in repairing damaged cartilage and/or in treating a subject having a disorder characterized by damage or loss of cartilage.

In some embodiments of any one of the embodiments of any of the aspects described herein, the composition and/or medicament is identified for use in arthroscopic surgery.

In some embodiments of any one of the embodiments of any of the aspects described herein, the method and/or use is effected by arthroscopic surgery.

As used herein, the phrase "arthroscopic surgery" refers to a minimally invasive surgical procedure in which treatment of damage of the interior of a joint is performed through a small incision.

Without being bound by any particular theory, it is believed that the fluidity of compositions described herein renders them particularly suitable for injection through a small incision such as used in arthroscopic surgery, whereas their viscosity and ability to be cured renders them particularly suitable for remaining in a desired location during and after surgery.

Examples of conditions associated with damage or loss of cartilage which may be treated according to embodiments of the invention, including by embodiments involving arthroscopic surgery, include torn floating cartilage, torn surface cartilage, and torn and/or reconstructed anterior cruciate ligament.

In some embodiments of any one of the embodiments of any of the aspects described herein, the composition is curable by polymerization (e.g., as described herein) in a physiological medium. In some embodiments, the polymerization is initiated by irradiation (e.g., as described herein).

Without being bound by any particular theory, it is believed that polymerization, and particularly polymerization initiated by irradiation, is an especially suitable (e.g., biocompatible) reaction mechanism for applications involving live tissue (e.g., in vivo applications), such as described herein, because a high degree of covalent cross-linking can be induced by only a relatively small amount of a reactive compound (e.g., an initiator), which may help to minimize toxicity or other adverse effects caused by chemical reactions. In addition, irradiation can be readily focused to a desired location (e.g., during surgery), thereby further minimizing adverse chemical reactions.

In some embodiments of any one of the embodiments described herein, the composition forms a hydrogel scaffold (e.g., as described herein) upon curing in the physiological medium.

In some embodiments of any one of the embodiments of any of the aspects described herein, the composition is prepared and/or stored at a temperature in which the composition is not a viscous fluid and/or gel such as described herein. Such a temperature may be, for example, a temperature (e.g., storage temperature) at which the composition is a frozen solid, or a temperature at which the composition is a relatively low-viscosity fluid (e.g., a temperature below a transition temperature as described herein).

In some embodiments of any one of the embodiments described herein, the composition is subjected to a temperature (e.g., a temperature above a transition temperature as described herein) at which the composition is converted to a viscous fluid and/or gel such as described herein (e.g., by undergoing reverse thermal gelation). The composition may be determined as being converted to the viscous fluid and/or gel state by visual inspection of an appearance of the composition (e.g., the composition appears cloudy) and/or by assessing a consistency (e.g., viscosity) of the composition (e.g., by inverting and/or shaking the composition).

Additional Ingredients, Packaging and Kits:

Any of the compositions according to any one of the embodiments described herein may be formulated for facilitating its administration (e.g., implantation).

In some embodiments of any one of the embodiments described herein, any of the compositions described herein may further comprise a pharmaceutically acceptable carrier.

Herein, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

In some embodiments of any one of the embodiments described herein, the carrier is an aqueous carrier, for example, an aqueous solution (e.g., saline). Phosphate buffer saline is an exemplary aqueous carrier which may optionally be used in some embodiments of any one of the embodiments described herein.

In some embodiments of any one of the embodiments described herein, a pH of the aqueous carrier is in a range of from 5 to 9. In some embodiments, the pH is in a range of from 6 to 8. In some embodiments, the pH is in a range of from 7 to 7.5.

In some embodiments of any one of the embodiments described herein, a pH of the aqueous carrier is about 7.4.

In some embodiments of any one of the embodiments described herein, any of the compositions described herein is packaged in a packaging material and identified in print, in or on the packaging material, for use in repairing tissue damage, inducing formation of tissue and/or for treating a subject having a disorder, as described herein.

In some embodiments of any one of the embodiments described herein, any of the compositions-of-matter described herein is packaged in a packaging material and identified in print, in or on the packaging material, for use in repairing tissue damage, inducing formation of tissue and/or for treating a subject having a disorder, as described herein.

In some embodiments of any one of the embodiments described herein, the composition is formulated for being stored under temperatures below 0° C., for example, at approximately −20° C.

In some embodiments of any one of the embodiments described herein, the composition is packaged in a partially or completely opaque container (e.g., a container which forms a part of an applicator described herein), so as to minimize a risk of premature photoinitiation of polymerization.

The composition described herein may also be provided as part of a kit.

Thus, according to another aspect of embodiments of the invention, there is provided a kit comprising any of the compositions described herein.

In some embodiments of any one of the embodiments described herein, the kit comprises an applicator loaded with the composition, the applicator being configured for releasing the composition as a result of pressure applied to the composition. As exemplified herein, even a highly viscous state of the composition may be fluid under pressure.

Pressure on the composition may be caused, for example, by manual pressure, by a compressed gas within the applicator, and/or by a motor (e.g., electric motor).

In some embodiments, the applicator comprises a piston (e.g., as in a syringe) configured for applying pressure to the composition in the applicator.

In some embodiments, the conjugate, poloxamer and substituted poloxamer (as described herein) are stored separately (e.g., in a form of a composition such as described herein) from a free radical initiator (as described herein) within a kit, for example, in separate packaging units, such that the composition is stored without including an initiator, until being contacted with the initiator shortly prior to cross-linking, as described herein. Such storage of the components of the composition prior to use may help to prevent premature initiation of cross-linking of components of the composition.

In some embodiments of any one of the embodiments described herein, the conjugate, poloxamer and substituted poloxamer (as described herein) are stored separately from a carrier (as described herein) within a kit, for example, in separate packaging units, such that the conjugate, poloxamer and substituted poloxamer are stored in a dry state until being contacted with the carrier for formation of a composition comprising a carrier as described herein. Such storage of the components of the composition prior to use may increase an effective life span of the components (and kit).

In some embodiments of any one of the embodiments described herein, the kit further comprises instructions providing guidance with regard to storage and/or use of the composition therein.

In some embodiments of any one of the embodiments described herein, the kit comprises instructions providing guidance with regard to selecting the cross-linking conditions (e.g., with or without irradiation; with or without heating; with or without adding a polymerization initiator) for obtaining a composition-of-matter with desired properties.

In some embodiments of any one of the embodiments described herein, the kit comprises instructions providing guidance with regard to when the composition is ready for use (e.g., as described herein), for example, how to determine when sufficient reverse thermal gelation has occurred (e.g., as described herein).

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials and Methods

Materials:

Irgacure® 2959 was obtained from Ciba.

F127 poloxamer-diacrylate (F127-DA) and poly(ethylene glycol)-diacrylate (PEG-DA) were prepared by acrylation of Pluronic® F127 (12.6 kDa) and poly(ethylene glycol) (PEG) diol (12 kDa), respectively, as described in International Patent Application PCT/IL2010/001072 (published as WO2011/073991).

F127 poloxamer-fibrinogen and PEG-fibrinogen conjugates were prepared from F127-DA and PEG-DA, respectively, as described in International Patent Application PCT/IL2010/001072 (published as WO2011/073991).

Rheological Measurements:

Rheological measurements were carried out using an AR-G2 rheometer (TA Instruments, New Castle, Del., USA) equipped with a Peltier plate temperature-controlled base. A 20 mm stainless steel plate geometry was used in all experiments. Each measurement was carried out with 0.2 ml of a polymer solution containing 0.1% (w/v) Irgacure® 2959 initiator. The testing conditions for the rheological measurements were 2% strain at an oscillation frequency of 3 radians per second.

The reverse thermal gelation of non-cross-linked formulations was assessed by temperature-dependent rheology measurements. The effects of cross-linking on formulation rheology were assessed by cross-linking formulations while performing time-dependent rheology measurements.

Statistical Analysis:

Statistical analysis was performed using Microsoft Excel statistical analysis software. Comparisons between two treatments were made using a student's T-test (two-tailed, equal variance). A p-value of <0.05 was considered to be statistically significant.

Example 1

Effect of Poloxamer on Properties of PEG-Fibrinogen Formulations

Various formulations for hydrogel precursor solutions were prepared by dissolving PEG-DA (PEG-diacrylate), F127-OH (F127 poloxamer), F127-Da (F127 poloxamer-diacrylate) and/or F127-MA (F127 poloxamer monoacrylate) at indicated concentrations and 0.1% (w/v) Irgacure® 2959 in a solution of 7.3 mg/ml PEG-fibrinogen in phosphate buffer saline (PBS) at a pH of 7.4. The mixtures were kept at a temperature of 4° C. until complete dissolution was observed.

Hydrogel precursor solutions were cross-linked by irradiating the precursor solution with UV light (365 nm, 4-5 mW/cm$^2$), to form hydrogels. A volume of 100 µl hydrogel precursor solution was irradiated in a 5 mm diameter silicon tube, resulting in 5 mm tall hydrogel cylinders.

For each formulation, the rheological properties (e.g., shear storage modulus (G')) of the hydrogel precursor solutions (i.e., prior to UV cross-linking) and hydrogels (i.e., after UV cross-linking) were measured as described hereinabove.

Swelling was calculated as the percent increase in weight of hydrogels swollen with phosphate buffered saline (PBS) over the initial weight of the hydrogels.

The shear storage modulus (G') values and swelling ratios obtained with the various formulations are summarized in Table 1 below.

As shown in Table 1, the various forms of F127 poloxamer (F127-OH, F-127-MA and F127-DA) were each effective at increasing G' values prior to cross-linking, whereas PEG-DA decreased G' values prior to cross-linking (compare, for example, Formulations 4 and 7). Non-acrylated and mono-acrylated polymers (F127-OH and F127-MA) were considerably more effective at increasing G' values prior to cross-linking than were diacrylated polymers (compare, for example, Formulation 2 with Formulations 3 and 4, Formulation 5 with Formulation 7, and Formulation 6 with Formulation 10).

As further shown therein, diacrylated polymers (PEG-DA and F127-DA) were highly effective at increasing G' values of cross-linked hydrogels (compare, for example, Formulation 2 with Formulations 3 and 4, Formulation 4 with Formulation 7, and Formulation 7 with Formulation 10).

TABLE 1

Composition and physical properties of exemplary formulations before and after cross-linking

| Formulation No. | Components (in addition to 7.3 mg/ml PEG-fibrinogen) | | | | Physical Properties | | |
|---|---|---|---|---|---|---|---|
| | PEG-DA (%) | F127-OH (%) | F127-DA (%) | F127-MA (%) | Swelling (%) | G' at 17° C. prior to UV cross-linking (Pa) | G' at 17° C. after UV cross-linking (Pa) |
| 1 | 5 | 0 | 0 | 0 | 43 | ~0 | 5000 |
| 2 | 5 | 23 | 0 | 0 | 210 | 8000 | 27000 |
| 3 | 5 | 19.8 | 3.8 | 0 | 150 | ~0 | 45000 |
| 4 | 5 | 15.4 | 7.6 | 0 | 90 | ~0 | 60000 |
| 5 | 0 | 15.4 | 0 | 7.6 | 137 | 10000 | 35000 |
| 6 | 0 | 12 | 0 | 8 | 108 | 100 | 24000 |
| 7 | 0 | 15.4 | 7.6 | 0 | 94 | 100 | 37000 |
| 8 | 0 | 12 | 8 | 0 | 66 | 2 | 40000 |
| 9 | 0 | 15.9 | 8.1 | 0 | 93 | 13000 | 47000 |
| 10 | 0 | 15.4 | 8.1 | 0 | 80 | 12000 | 44000 |

Compositions which exhibited relatively high viscosity (e.g., a relatively high G' value) prior to cross-linking were advantageously easier to handle at about room temperature, due to their reduced fluidity.

In addition, it was hypothesized that excessive swelling of a cross-linked formulation may result in deleterious effects, so a degree of swelling which is not much more than that of Formulation 1 (which experience has shown to be satisfactory with respect to its swelling properties) was considered to be advantageous. A presence of F127-DA was associated with lower degrees of swelling (compare, for example, Formulation 2 with Formulation 3, Formulation 3 with Formulation 4, and Formulation 7 with Formulations 5 and 10).

Taken together, the above results show that a combination of F127-OH and F127-DA, at sufficiently high concentrations in a PEG-fibrinogen-comprising composition (e.g., as in Formulations 9 and 10), result in swelling of less than 100%, a G' of at least 10,000 Pa prior to cross-linking, and a G' of at least 40,000 Pa after cross-linking.

Example 2

Properties of Exemplary Formulation Comprising PEG-Fibrinogen with Acrylated and Non-Acrylated F127 Poloxamer Formulation 10, comprising 7.3 mg/ml PEG-fibrinogen, 15.4 weight percents F127-OH and 8.1 weight percents F127-DA (as described in Example 1), was selected for further characterization of its physical and chemical properties. Formulation 10 was expected to be particularly advantageous because it exhibited considerable viscosity prior to cross-linking, while exhibiting less swelling following cross-linking than similarly viscous formulations.

The shear storage modulus (G') of Formulation 10 (as a non-cross-linked solution) was measured as a function of temperature, as described in the Materials and Methods section. For comparison a formulation comprising 7.4 mg/ml PEG-fibrinogen and 10 weight percents F127-DA was also measured.

As shown in FIG. 1, Formulation 10 undergoes a transition at about 16° C., characterized by a sharp increase in G'. In contrast, a solution of 7.4 mg/ml PEG-fibrinogen with 10 weight percents F127-DA exhibited no such increase in G'.

Figure 2A:
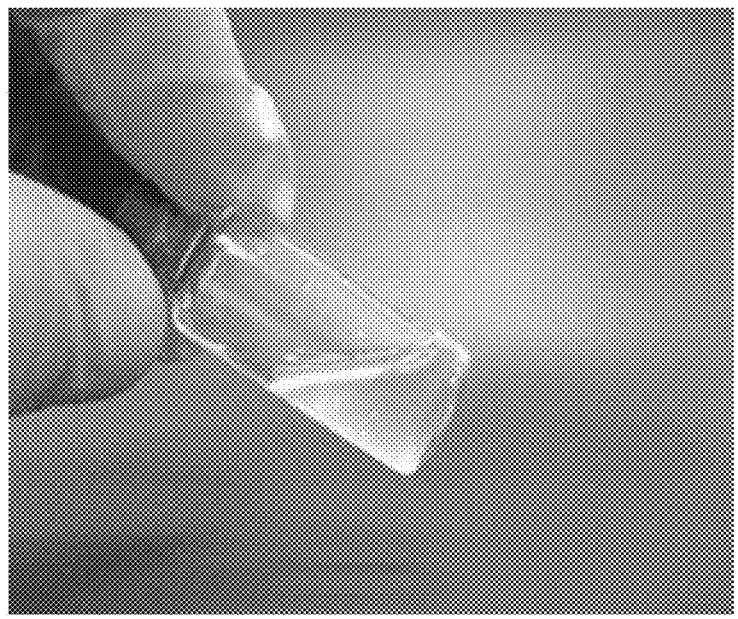
FIGS. 2A-2B are images showing an exemplary composition exhibiting fluidity at 4° C.
Figure 2B:

As shown in FIGS. 2A and 2B, Formulation 10 was a free flowing liquid at a temperature of 4° C. (FIG. 2A), but was sufficiently viscous at room temperature so as not to exhibit flow over short time ranges (FIG. 2B).

The hydrogel precursor solution of Formulation 10 was readily drawn in to a syringe at low temperature, as it was a free flowing liquid at such a temperature.

Figure 3:
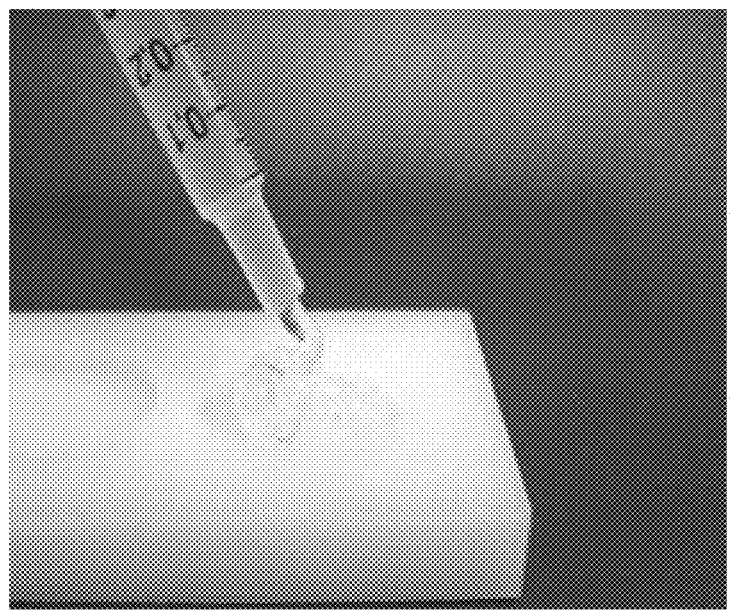
FIG. 3 is an image showing injection of an exemplary composition via syringe at room temperature.

As shown in FIG. 3, the solution was injected from a syringe at room temperature, in the form of a viscous material.

Figure 4:
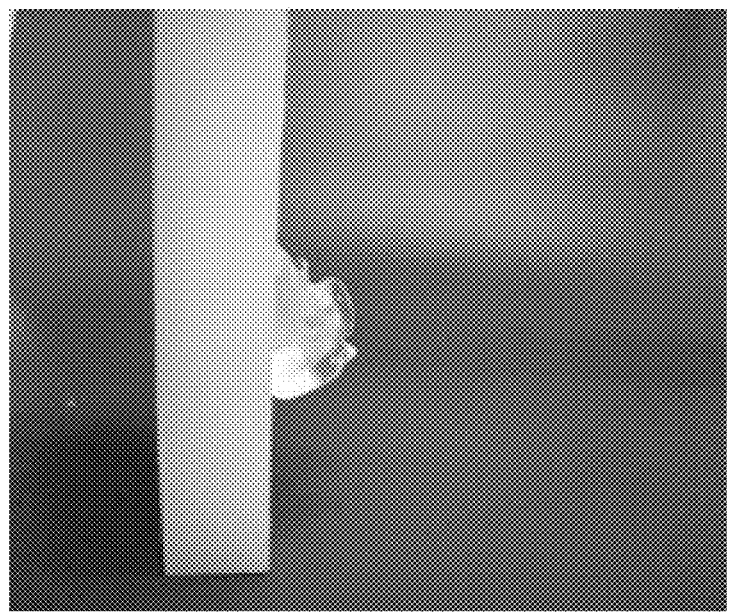
FIG. 4 is an image showing adherence of an exemplary composition to a vertical surface at room temperature.
Figures 5A, 5B, 5C, 5D:
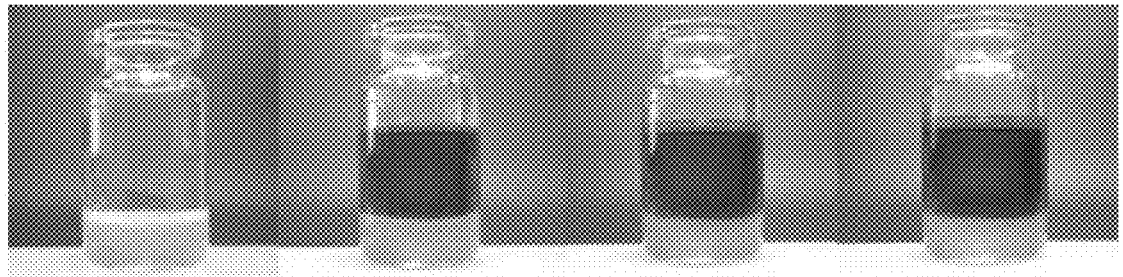
FIGS. 5A-5D are images showing an exemplary composition (grey bottom layer) prior to (FIG. 5A), immediately after (FIG. 5B) is a, 1 hour after (FIG. 5C) and two hours after (FIG. 5D) incubation with an aqueous dye solution (dark upper layer)

As shown in FIG. 4, the injected viscous material could adhere to a vertical surface without flowing downward.

These results indicate that the physical properties of such formulations result in a free flowing liquid at low temperatures for convenient handling (e.g., loading into a syringe), as well as a viscous material at room temperature which is both injectable and capable of remaining in a target site regardless of spatial orientation of the target site.

In order to evaluate the ability of the formulation to resist water, the viscous material was incubated with an aqueous dye solution for two hours.

As shown in FIGS. 5A-5D, the viscous material exhibits substantially no absorption of water or water-soluble dye, even after incubation with an aqueous dye solution for 2 hours.

In order to quantitatively evaluate the resistance of the formulation to dissolution in an aqueous environment, about 1 ml of Formulation 10 was placed in a 2 ml serum glass vial (Wheaton). The formulation was exposed to a temperature of 20° C., at which the formulation was in a viscous form, and 1 ml of PBS buffer (pH 7.4) was then poured above the formulation. This configuration created an interface of between the viscous formulation and the PBS, with an area of 38.48 $mm^2$. The initial weight of the formulation was measured and the final weight (after exposure to the aqueous environment) of the formulation were measured after 1 or 2 hours (3 samples were measured at each time point). The change in weight of the formulation was normalized to change in weight per 1 cm².

Figure 6:
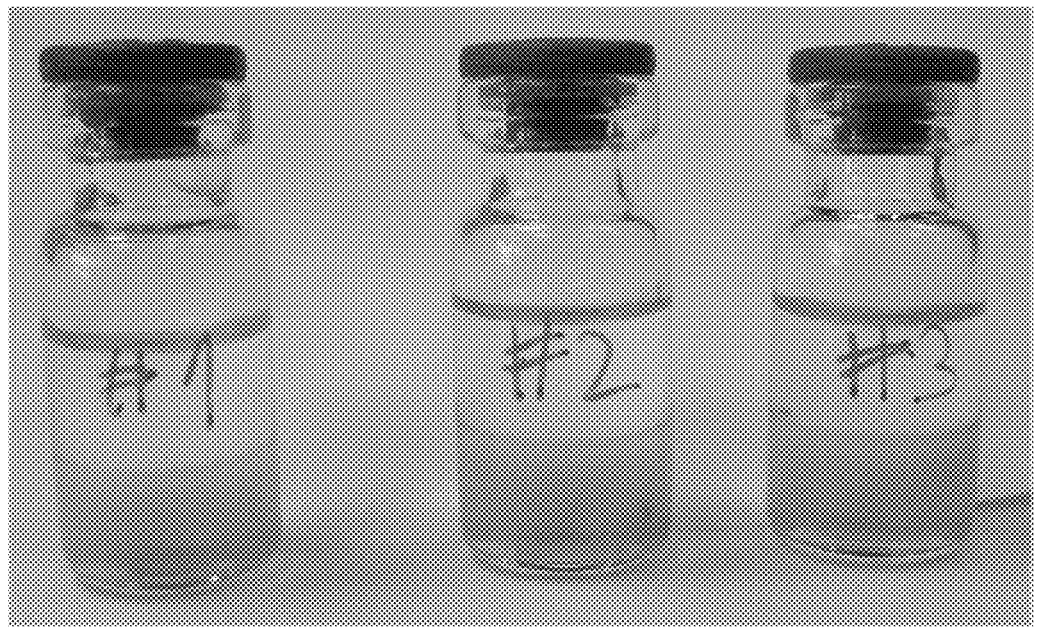
FIG. 6 presents an image showing an exemplary composition to which indigo carmine was added for visualization (dark bottom layer) incubated with an aqueous solution (transparent upper layer)
Figure 7A:
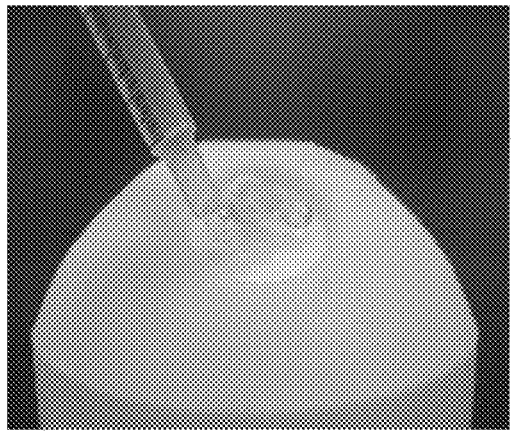
FIGS. 7A-7D are images showing injection of an exemplary composition into an artificial lesion (FIG. 7A), the composition filling the artificial lesion (FIG. 7B), UV irradiation for cross-linking the composition (FIG. 7C), and a hydrogel formed by cross-linking the composition (FIG. 7D)
Figure 7B:
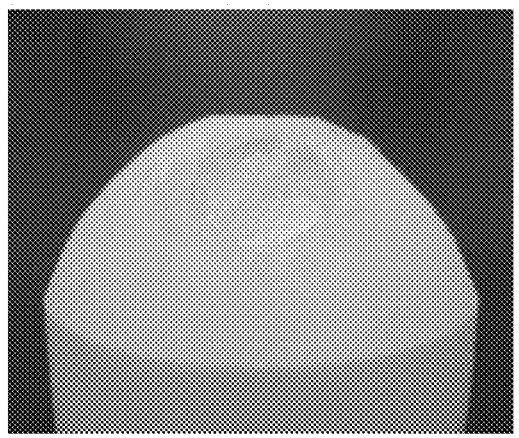
Figure 7C:
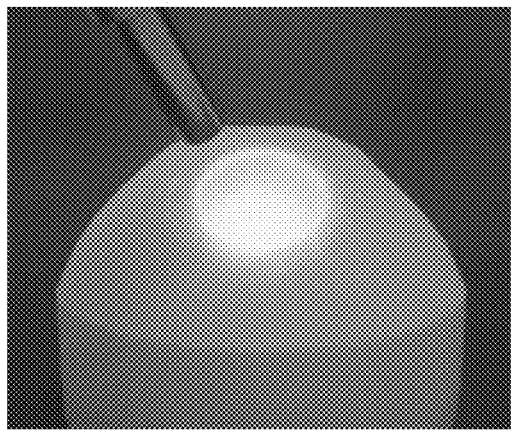
Figure 7D:
Figure 8A:
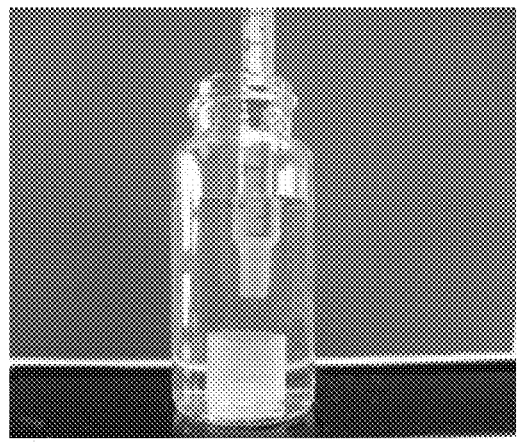
FIGS. 8A-8D are images showing underwater injection of an exemplary composition into a cylindrical mold at 21° C.
Figure 8B:
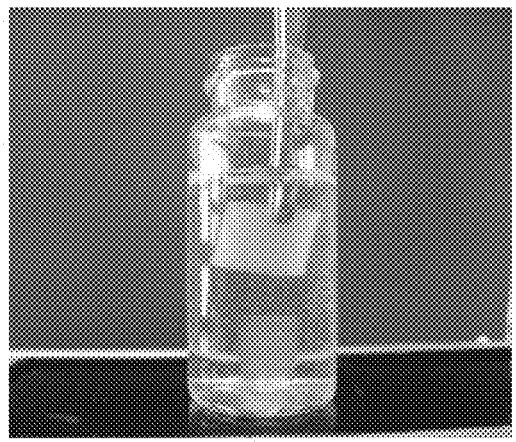
Figure 8C:
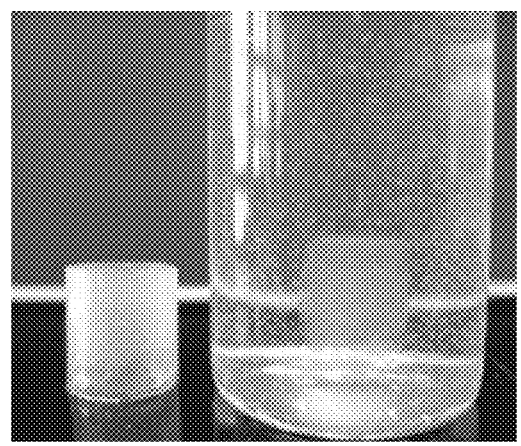
Figure 8D:
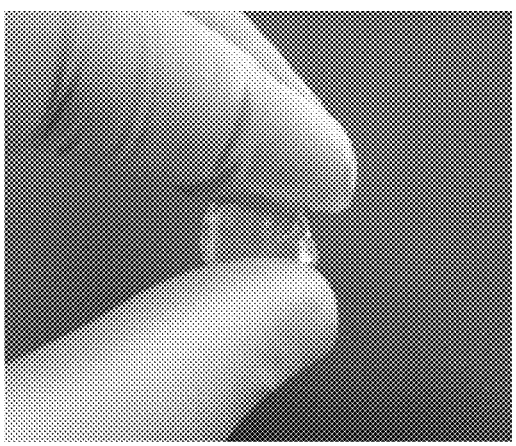

As shown in Table 2 below and in FIG. 6, the formulation dissolved at a rate of only about 34 mg/cm² per hour over the course of two hours exposure to an aqueous environment.

This result indicates that the formulation is water-resistant, that is, it is not substantially affected by contact with water within a short time period, and can therefore be used in aqueous environments such as in the body, while retaining its viscous properties.

TABLE 2

| | Change in weight of Formulation 10 upon exposure to PBS | | | | | | |
|---|---|---|---|---|---|---|---|
| | | 1 hour exposure to PBS | | | 2 hours exposure to PBS | | |
| Sample No. | Initial weight (mg) | Final weight (mg) | Weight change (mg) | Weight change per cm² (mg) | Final weight (mg) | Weight change (mg) | Weight change per cm² (mg) |
| 1 | 849.1 | 841.6 | −7.5 | −19.5 | | | |
| 2 | 977.3 | 964.7 | −12.6 | −32.7 | | | |
| 3 | 928.0 | 918.4 | −9.6 | −24.9 | | | |
| Average of 1-3 | | | −9.9 ± 2.6 | −25.7 ± 6.7 | | | |
| 4 | 807.5 | | | | 781.7 | −25.8 | −67.0 |
| 5 | 882.3 | | | | 853.6 | −28.7 | −74.6 |
| 6 | 996.8 | | | | 973.3 | −23.5 | −61.1 |
| Average of 4-6 | | | | | | −26.0 ± 2.6 | −67.6 ± 6.8 |

Example 3

Cross-Linking of Exemplary Formulation Comprising PEG-Fibrinogen with Acrylated and Non-Acrylated F127 Poloxamer In order to evaluate the utility of Formulation 10, as described in Examples 1 and 2, for implantation and cross-linking in situ, the formulation was placed in an artificial lesion and cross-linked by UV irradiation at a wavelength of 365 nm.

As shown in FIGS. 7A-7D, the consistency of the formulation allowed for injection of the formulation into the artificial lesion and molding of the formulation to fit the shape of the lesion, and UV irradiation resulted in a hydrogel with a relatively solid consistency, which fit the shape of the lesion.

Furthermore, as shown in FIGS. 8A-8D, the formulation could be injected into a mold within an aqueous environment, and cross-linked to produce a hydrogel in the shape of the mold.

These results confirm that the formulation can be applied by injection and cross-linked in situ to produce a hydrogel, even in aqueous environments such as in the body.

Example 4

Effect of PEG-Fibrinogen Concentration of Formulation Properties

In order to evaluate the effect of PEG-fibrinogen concentration on the properties of formulations before and after cross-linking, the above-described Formulation 10 was modified so as to contain 0, 4, 7 or 10 mg/ml of PEG-fibrinogen.

The rheology of formulations was measured as described in the Materials and Methods section hereinabove.

Figure 9:
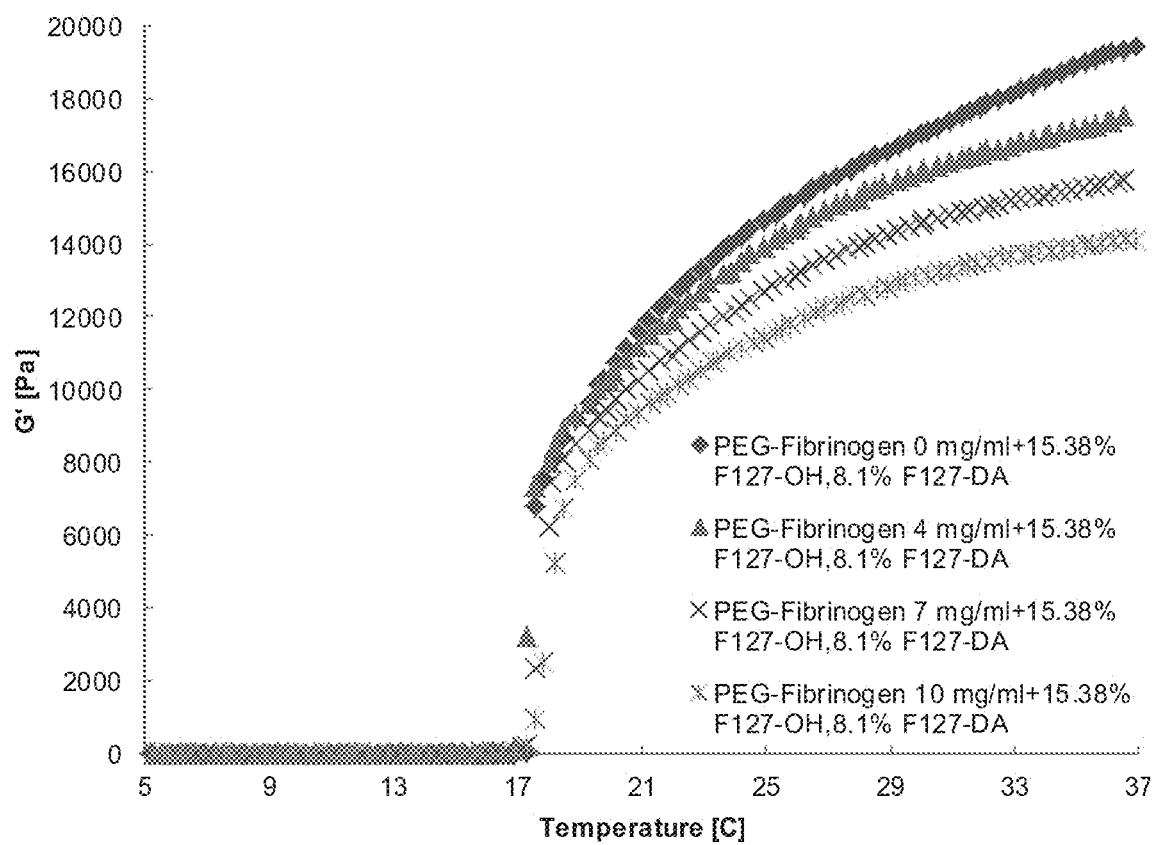
FIG. 9 is a graph showing the shear storage modulus (G') as a function of temperature for exemplary compositions with 0, 4, 7 or 10 mg/ml PEG-fibrinogen.

As shown in FIG. 9, higher concentrations of PEG-fibrinogen in the formulation were associated with lower G' values upon reverse thermal gelation, and with slightly higher gelation temperatures.

These results indicate that the PEG-fibrinogen acts like a plasticizer, and decreases the degree of reverse thermal gelation as compared with F127-OH and F127-DA alone.

Figure 10:
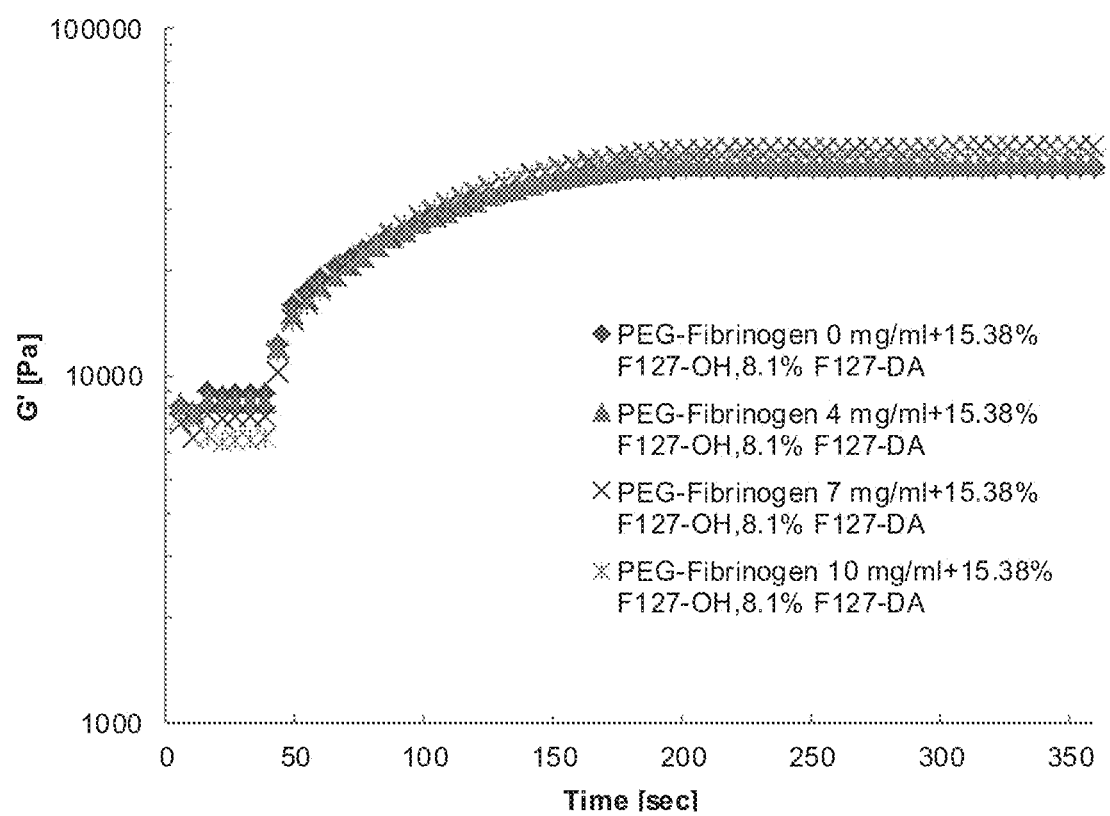
FIG. 10 is a graph showing the change in shear storage modulus (G') upon cross-linking of exemplary compositions with 0, 4, 7 or 10 mg/ml PEG-fibrinogen.

As shown in FIG. 10, higher concentrations of PEG-fibrinogen in the formulation were associated with higher G' values upon cross-linking.

These results suggest that PEG-fibrinogen increases cross-linking density, thereby resulting in a stiffer hydrogel.

Example 5

Comparison of PEG-Fibrinogen and Poloxamer-Fibrinogen in Formulations

In order to evaluate the effect on of the polymer conjugated to the protein on formulation properties, a new formulation ("Formulation 11") was prepared which comprised an F127 poloxamer-fibrinogen instead of PEG-Fibrinogen as in Formulation 10. Formulations 10 and 11 were otherwise identical, comprising 7.3 mg/ml PEG-fibrinogen or F127-fibrinogen, 15.4 weight percents F127-OH and 8.1 weight percents F127-DA. The rheology of Formulations 10 and 11 were measured as described in the Materials and Methods section hereinabove.

Figure 11:
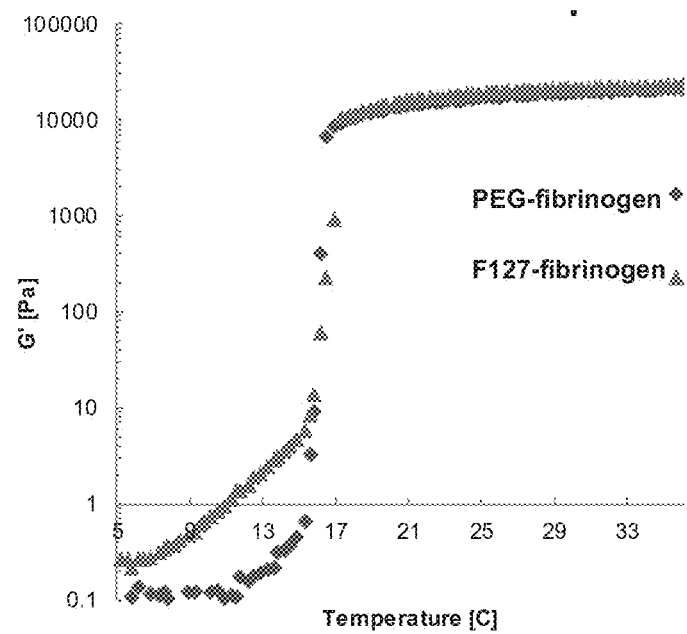
FIG. 11 is a graph showing the shear storage modulus (G') as a function of temperature for exemplary compositions with 7.3 mg/ml PEG-fibrinogen or F127-fibrinogen, 15.4% F127 poloxamer, and 8.1% F127 poloxamer-diacrylate.

As shown in FIG. 11, replacing PEG-fibrinogen with F127-fibrinogen did not affect either the properties of the gel upon reverse thermal gelation or the gelation temperatures. However, F127-fibrinogen resulted in somewhat higher G' values at low temperature (in the absence of reverse thermal gelation).

Figure 12:
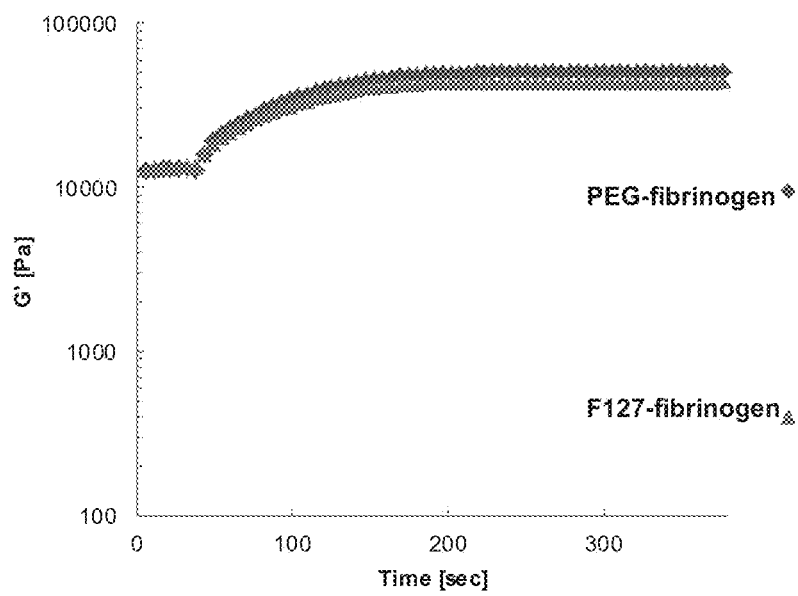
FIG. 12 is a graph showing the change in shear storage modulus (G') upon cross-linking of exemplary compositions with 7.3 mg/ml PEG-fibrinogen or F127-fibrinogen, 15.4% F127 poloxamer, and 8.1% F127 poloxamer-diacrylate.

As shown in FIG. 12, replacing PEG-fibrinogen with F127-fibrinogen did not significantly affect the properties of the cross-linked hydrogel.

These results indicate that the identity of the polymer conjugated to the protein is not a significant factor in determining the rheological properties of the formulations either prior to cross-linking or after cross-linking.

Example 6

Hydrolytic and Proteolytic Degradation of Hydrogels

Formulations 10 and 11 were prepared and cross-linked as described hereinabove. The formulations were cross-linked in 16 mm diameter Teflon molds, by UV irradiation (365 nm, 5 mW/cm$^2$) for 5 minutes, resulting in a disk-shaped hydrogel.

In order to evaluate the susceptibility of the hydrogels to hydrolytic degradation, hydrogel samples were immersed in 50 ml of PBS (phosphate buffer saline) at a temperature of 50° C. At various time points, the samples were washed thrice with 50 ml of cold (4° C.) DDW (double-distilled water) in order to remove residual material from the hydrogel. The samples were then frozen and lyophilized for 24 hours, and their dry mass values were obtained. The mass loss percentages represented the level of hydrolytic degradation.

In order to evaluate the susceptibility of the hydrogels to proteolytic degradation, the hydrogel samples were immersed for 24 hours in PBS containing 0.1 weight percent trypsin at a temperature of 37° C. The samples were then washed, frozen and lyophilized as described hereinabove, and protein concentration was then determined using a Kjeldahl nitrogen determination system.

Figure 13:
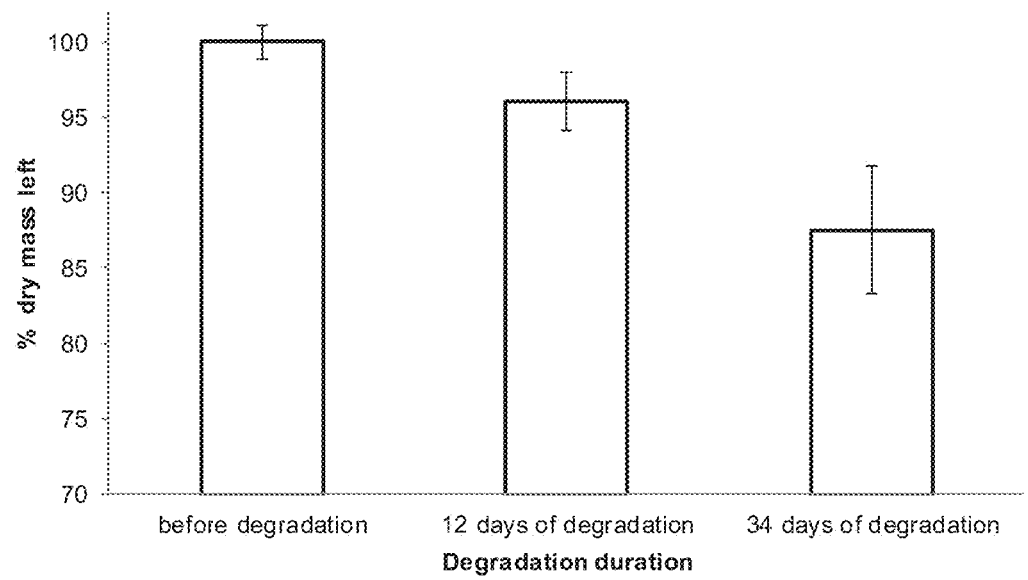
FIG. 13 is a bar graph showing the change in dry mass of an exemplary hydrogel following 12 or 34 days of incubation in PBS (pH 7.4) at 50° C.

As shown in FIG. 13, approximately 15% of the hydrogel degraded after 34 days in PBA at 50° C. This result indicates that the hydrogel is susceptible to hydrolysis.

Figure 14:
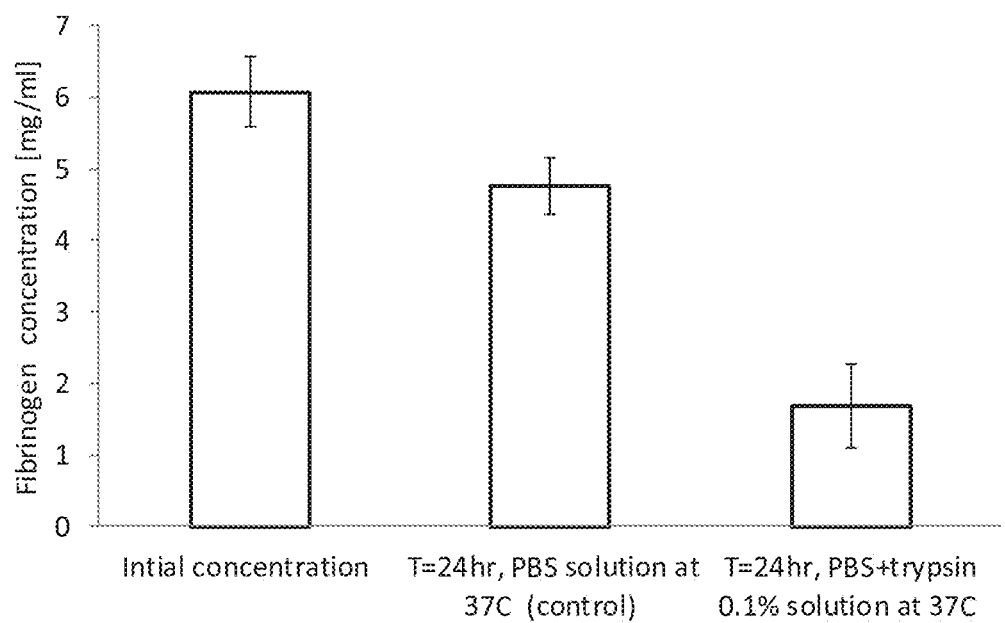
FIG. 14 is a bar graph showing the change in fibrinogen concentration in an exemplary hydrogel following 24 hours of incubation in PBS, with and without 0.1% trypsin, at 37° C.

As shown in FIG. 14, incubation with trypsin resulted in rapid degradation of the hydrogel. This result indicates that cleavage of peptide bonds in the fibrinogen results in degradation of the hydrogel.

The above results indicate that hydrogels prepared by cross-linking of formulations described herein are biodegradable, being degraded by both hydrolysis (apparently due to hydrolysis of ester bonds) and proteolysis. Following degradation, the degradation products diffuse out of the cross-linked matrix. In addition, the F127-OH in the hydrogel is not covalently bound, and can diffuse out of the cross-linked matrix in an aqueous environment.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A pharmaceutical, cosmetic or cosmeceutical composition comprising:
    (a) a polymer-polypeptide conjugate comprising a polypeptide having attached thereto at least two polymeric moieties, said polypeptide comprising an extracellular matrix protein or a fragment thereof, wherein at least one of said polymeric moieties further comprises at least one polymerizable group, wherein molecules of said conjugate are not covalently linked to one another;
    (b) an F127 poloxamer;
    (c) an F127 poloxamer substituted by at least one polymerizable group; and
    (d) a pharmaceutically, cosmetically or cosmeceutically acceptable carrier, wherein the concentration of the F127 poloxamer is at least 12 weight percents, and the total concentration of said F127 poloxamer and said F127 poloxamer substituted by at least one polymerizable group is at least 22 weight percents, wherein the composition exhibits a reverse thermal gelation, and wherein a shear storage modulus of the composition is at least 10,000 Pa at a temperature of 17° C., and less than 100 Pa at a temperature of 4° C.

2. The composition of claim 1, wherein said shear storage modulus is no more than 20000 Pa at a temperature of 17° C.

3. The composition of claim 1, wherein said shear storage modulus is less than 10 Pa at a temperature of 4° C.

4. The composition of claim 1, wherein the composition has a dissolution rate of less than 50 mg/cm$^2$ per hour in an aqueous environment.

5. The composition of claim 1, wherein the concentration of said conjugate is in a range of from 2 to 15 mg/ml.

6. The composition of claim 1, wherein the concentration of said F127 poloxamer is in a range of from 13 to 25 weight percents.

7. The composition of claim 1, wherein the concentration of said F127 poloxamer substituted by at least one polymerizable group is in a range of from 7.8 to 15 weight percents.

8. The composition of claim 1, wherein said conjugate has the general formula:

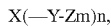

wherein:
X is said polypeptide;
Y is said polymeric moiety;
Z is said polymerizable group;
n is an integer greater than 1; and
m is 1 or an integer greater than 1.

9. The composition of claim 1, wherein said polypeptide comprises a fibrinogen or a fragment thereof.

10. The composition of claim 1, wherein each of said polymeric moieties comprises a synthetic polymer.

11. The composition of claim 10, wherein said synthetic polymer is selected from the group consisting of a poly (ethylene glycol) and a poloxamer (poly(ethylene glycol-propylene glycol) copolymer).

12. The composition of claim 1, wherein said polymerizable group is polymerizable by free radical polymerization.

13. The composition of claim 1, wherein said polypeptide is denaturated fibrinogen and each of said polymeric moieties comprises poly(ethylene glycol) and/or F127 poloxamer.

14. The composition of claim 1, further comprising a free radical initiator.

15. The composition of claim 1, wherein said reverse thermal gelation has a transition temperature in a range of from 10° C. to 17° C.

16. The composition of claim 1, wherein said reverse thermal gelation of said composition increases a shear storage modulus of said composition by at least ten-folds.

17. The composition of claim 1, wherein the composition has a shear storage modulus in a range of from 10,000 Pa to 15,000 Pa at a temperature of 17° C.

18. A kit comprising the composition of claim 1.

19. The kit of claim 18, further comprising instructions for use in repairing tissue damage and/or instructions for use in treating a subject having a disorder characterized by tissue damage or loss.

20. A composition-of-matter comprising a cross-linked form of the composition of claim 1, said cross-linked form comprising a plurality of molecules of said conjugate and said poloxamer substituted by at least one polymerizable group covalently cross-linked to one another upon polymerization of said polymerizable group.

21. The composition-of-matter of claim 20, being a scaffold.

22. The composition-of-matter of claim 20, being a hydrogel.

23. The composition-of-matter of claim 20, being characterized by a shear storage modulus of at least 30,000 Pa at a temperature of 17° C.

24. A process of producing a composition-of-matter comprising a plurality of molecules of a polymer-polypeptide conjugate and a poloxamer substituted by at least one polymerizable group being covalently cross-linked to one another upon polymerization of said polymerizable group, the process comprising subjecting a composition as described in claim 1 to conditions that effect covalent cross-linking by polymerization of said polymerizable group, thereby producing the composition-of-matter.

25. The process of claim 24, wherein said covalent cross-linking is effected in vivo.

26. The process of claim 24, wherein said conditions comprise irradiation.

27. A method of inducing formation of a tissue in vivo, the method comprising implanting the composition-of-matter of claim 20 in a subject, to thereby induce the formation of the tissue.

28. A method of inducing formation of a tissue in vivo, the method comprising administering the composition of claim 1 to a subject, and subjecting the composition to conditions that effect covalent cross-linking by polymerization of said polymerizable group, to thereby induce the formation of the tissue.

29. A method of treating a subject having a disorder characterized by tissue damage or loss, the method comprising implanting the composition-of-matter of claim 20 in a subject, to thereby induce formation of said tissue, thereby treating the disorder characterized by tissue damage or loss.

30. A method of treating a subject having a disorder characterized by tissue damage or loss, the method comprising administering to the subject the composition of claim 1, and subjecting the composition to conditions that effect covalent cross-linking by polymerization of said polymerizable group, to thereby induce formation of said tissue, thereby treating the disorder characterized by tissue damage or loss.

31. The method of claim 30, wherein said tissue comprises cartilage.

* * * * *